US010238647B2

(12) United States Patent
Weber et al.

(10) Patent No.: US 10,238,647 B2
(45) Date of Patent: Mar. 26, 2019

(54) COMPOSITIONS FOR AFFECTING WEIGHT LOSS

(71) Applicant: Orexigen Therapeutics, Inc., La Jolla, CA (US)

(72) Inventors: Eckard Weber, San Diego, CA (US); Michael Alexander Cowley, Portland, OR (US)

(73) Assignee: Nalpropion Pharmaceuticals, Inc., Morristown, NJ (US)

( * ) Notice: Subject to any disclaimer, the term of this patent is extended or adjusted under 35 U.S.C. 154(b) by 0 days.

(21) Appl. No.: 15/276,600

(22) Filed: Sep. 26, 2016

(65) Prior Publication Data

US 2017/0007598 A1 Jan. 12, 2017

Related U.S. Application Data

(63) Continuation of application No. 14/602,154, filed on Jan. 21, 2015, now abandoned, which is a continuation of application No. 13/241,023, filed on Sep. 22, 2011, now abandoned, which is a continuation of application No. 12/751,970, filed on Mar. 31, 2010, now abandoned, which is a continuation of application No. 11/779,008, filed on Jul. 17, 2007, now abandoned, which is a continuation of application No. 10/828,795, filed on Apr. 21, 2004, now Pat. No. 7,375,111.

(60) Provisional application No. 60/466,838, filed on Apr. 29, 2003.

(51) Int. Cl.
| | |
|---|---|
| *A61P 3/04* | (2006.01) |
| *A61K 45/06* | (2006.01) |
| *A61K 31/135* | (2006.01) |
| *A61K 31/137* | (2006.01) |
| *A61K 31/138* | (2006.01) |
| *A61K 31/485* | (2006.01) |

(52) U.S. Cl.
CPC .......... *A61K 31/485* (2013.01); *A61K 31/135* (2013.01); *A61K 31/137* (2013.01); *A61K 31/138* (2013.01); *A61K 45/06* (2013.01); *A61P 3/04* (2018.01); *Y10S 514/909* (2013.01); *Y10S 514/964* (2013.01)

(58) Field of Classification Search
CPC .. A61K 31/485; A61K 31/465; A61K 31/135; A61K 31/00; A61P 3/04
USPC ...................................... 514/282, 649, 909
See application file for complete search history.

(56) References Cited

U.S. PATENT DOCUMENTS

| | | |
|---|---|---|
| 3,819,706 A | 6/1974 | Mehta |
| 3,885,046 A | 5/1975 | Mehta |
| 3,942,641 A | 3/1976 | Segre |
| 4,089,855 A | 5/1978 | Chatterjie et al. |
| 4,172,896 A | 10/1979 | Uno et al. |
| 4,218,433 A | 8/1980 | Kooichi et al. |
| 4,295,567 A | 10/1981 | Knudsen |
| 4,451,465 A | 5/1984 | White et al. |
| 4,483,846 A | 11/1984 | Koide et al. |
| 4,513,006 A | 4/1985 | Maryanoff et al. |
| 4,673,679 A | 6/1987 | Aungst et al. |
| 4,689,332 A | 8/1987 | McLaughlin et al. |
| 4,828,836 A | 5/1989 | Elger et al. |
| 4,831,031 A | 5/1989 | Lowe et al. |
| 4,855,306 A | 8/1989 | Markstein et al. |
| 4,895,845 A | 1/1990 | Seed |
| 5,000,886 A | 3/1991 | Lawter et al. |
| 5,028,612 A | 7/1991 | Glover |
| 5,082,864 A | 1/1992 | Van den Oetelaar et al. |
| 5,202,128 A | 4/1993 | Morella et al. |
| 5,213,807 A | 5/1993 | Chemburkar et al. |
| 5,213,808 A | 5/1993 | Bar-Shalom et al. |
| 5,283,263 A | 2/1994 | Norden |
| 5,312,925 A | 5/1994 | Allen et al. |
| 5,358,970 A | 10/1994 | Ruff et al. |
| 5,364,841 A | 11/1994 | Cooper et al. |
| 5,403,595 A | 4/1995 | Kitchell et al. |
| 5,426,112 A | 6/1995 | Zagon et al. |
| 5,427,798 A | 6/1995 | Ludwig et al. |
| 5,486,362 A | 1/1996 | Kitchell et al. |
| 5,512,593 A | 4/1996 | Dante |

(Continued)

FOREIGN PATENT DOCUMENTS

| | | |
|---|---|---|
| CA | 2317044 | 7/1999 |
| EP | 0 005 636 | 11/1979 |

(Continued)

OTHER PUBLICATIONS

Spiegel et al., "Effect of naltrexone on food intake, hunger, and satiety in obese men", Physiology & Behavior, vol. 40, No. 2, pp. 135-141 (1987).*

Blundell et al., "Serotonin and Appetite Regulation, Implications for the Pharmacological Treatment of Obesity", CNS Drugs, vol. 9, No. 6, pp. 473-495 (1998).*

Anonymous, Jun. 7, 2008, Orexigen® Therapeutics announces that Contrave® may reverse the incidence of metabolic syndrome, PipelinReview.com.

Anonymous, Nov. 24, 2013, Positive interim analysis of the light study, testing weight loss medication, Physicians' Academy for Cardiovascular Education-News, Orexigen press release.

(Continued)

*Primary Examiner* — Kevin E Weddington
(74) *Attorney, Agent, or Firm* — Servilla Whitney LLC

(57) ABSTRACT

Disclosed are compositions for affecting weight loss comprising a first compound and a second compound, where the first compound is an opioid antagonist and the second compound causes increased agonism of a melanocortin 3 receptor (MC3-R) or a melanocortin 4 receptor (MC4-R) compared to normal physiological conditions. Also disclosed are methods of affecting weight loss, increasing energy expenditure, increasing satiety in an individual, or suppressing the appetite of an individual, comprising identifying an individual in need thereof and treating that individual to antagonize opioid receptor activity and to enhance α-MSH activity.

17 Claims, No Drawings

(56) References Cited

U.S. PATENT DOCUMENTS

| | | |
|---|---|---|
| 5,541,231 A | 7/1996 | Ruff et al. |
| 5,626,874 A | 5/1997 | Conte et al. |
| 5,714,519 A | 2/1998 | Cincotta et al. |
| 5,716,976 A | 2/1998 | Bernstein |
| 5,719,197 A | 2/1998 | Kanios et al. |
| 5,731,000 A | 3/1998 | Ruff et al. |
| 5,738,874 A | 4/1998 | Conte et al. |
| 5,763,493 A | 6/1998 | Ruff et al. |
| 5,817,665 A | 10/1998 | Dante |
| 5,817,666 A | 10/1998 | Katz |
| 5,856,332 A | 1/1999 | Dante |
| 5,866,164 A | 2/1999 | Kuczynski et al. |
| 5,948,799 A | 9/1999 | Cropp |
| 5,958,962 A | 9/1999 | Cook |
| 5,977,099 A | 11/1999 | Nickolson |
| 6,004,970 A | 12/1999 | O'Malley et al. |
| 6,033,686 A | 3/2000 | Seth |
| 6,034,091 A | 3/2000 | Dante |
| 6,048,322 A | 4/2000 | Kushida |
| 6,071,537 A | 6/2000 | Shank |
| 6,071,918 A | 6/2000 | Cook |
| 6,087,386 A | 7/2000 | Chen et al. |
| 6,096,341 A | 8/2000 | Seth |
| 6,110,973 A | 8/2000 | Young |
| 6,120,803 A | 9/2000 | Wong et al. |
| 6,143,327 A | 11/2000 | Seth |
| 6,150,366 A | 11/2000 | Arenson et al. |
| 6,153,223 A | 11/2000 | Apelian et al. |
| 6,183,778 B1 | 2/2001 | Conte et al. |
| 6,191,117 B1 | 2/2001 | Kozachuk |
| 6,197,827 B1 | 3/2001 | Cary |
| 6,210,716 B1 | 4/2001 | Chen et al. |
| 6,238,697 B1 | 5/2001 | Kumar et al. |
| 6,245,766 B1 | 6/2001 | Watsky |
| 6,248,363 B1 | 6/2001 | Patel et al. |
| 6,262,049 B1 | 7/2001 | Coffin et al. |
| 6,274,579 B1 | 8/2001 | Morgan et al. |
| 6,294,192 B1 | 9/2001 | Patel et al. |
| 6,306,436 B1 | 10/2001 | Chungi et al. |
| 6,323,236 B2 | 11/2001 | McElroy |
| 6,342,496 B1 | 1/2002 | Jerussi et al. |
| 6,342,515 B1 | 1/2002 | Masuda et al. |
| 6,344,474 B1 | 2/2002 | Maruani et al. |
| 6,362,220 B1 | 3/2002 | Cottrell |
| 6,369,113 B2 | 4/2002 | Young |
| 6,383,471 B1 | 5/2002 | Chen et al. |
| 6,387,956 B1 | 5/2002 | Shapira |
| 6,420,369 B1 | 7/2002 | Marcotte |
| 6,437,147 B1 | 8/2002 | Andersen et al. |
| 6,441,038 B1 | 8/2002 | Loder et al. |
| 6,451,860 B1 | 9/2002 | Young |
| 6,462,237 B1 | 10/2002 | Gidwani et al. |
| 6,500,459 B1 | 12/2002 | Chhabra et al. |
| 6,506,799 B1 | 1/2003 | Dasseux |
| 6,514,531 B1 | 2/2003 | Alaux et al. |
| 6,528,520 B2 | 3/2003 | Clemens |
| 6,541,478 B1 | 4/2003 | O'Malley et al. |
| 6,548,551 B2 | 4/2003 | Hinz |
| 6,569,449 B1 | 5/2003 | Stinchcomb et al. |
| 6,576,256 B2 | 6/2003 | Liang et al. |
| 6,589,553 B2 | 7/2003 | Li et al. |
| 6,622,036 B1 | 9/2003 | Suffin |
| 6,627,223 B2 | 9/2003 | Percel et al. |
| 6,630,165 B2 | 10/2003 | Seroff et al. |
| 6,638,535 B2 | 10/2003 | Lemmens et al. |
| 6,652,882 B1 | 11/2003 | Odidi et al. |
| 6,682,759 B2 | 1/2004 | Lim et al. |
| 6,686,337 B2 | 2/2004 | Connor |
| 6,706,283 B1 | 3/2004 | Appel et al. |
| 6,713,488 B2 | 3/2004 | Sadee et al. |
| 6,797,283 B1 | 9/2004 | Edgren et al. |
| 6,893,660 B2 | 5/2005 | Li et al. |
| 6,893,661 B1 | 5/2005 | Odidi et al. |
| 6,905,708 B2 | 6/2005 | Li et al. |
| 6,923,988 B2 | 8/2005 | Patel et al. |
| 6,926,907 B2 | 8/2005 | Plachetka |
| 6,995,169 B2 | 2/2006 | Chapleo et al. |
| 7,109,198 B2 | 9/2006 | Gadde et al. |
| 7,375,111 B2 | 5/2008 | Weber et al. |
| 7,422,110 B2 | 9/2008 | Zanden et al. |
| 7,425,571 B2 | 9/2008 | Gadde et al. |
| 7,429,580 B2 | 9/2008 | Gadde et al. |
| 7,462,626 B2 | 12/2008 | Weber et al. |
| 7,682,633 B2 | 3/2010 | Matthews et al. |
| 7,754,748 B2 | 7/2010 | Gadde et al. |
| 8,088,786 B2 | 1/2012 | McKinney et al. |
| 8,318,788 B2 | 11/2012 | McKinney et al. |
| 8,722,085 B2 | 5/2014 | McKinney et al. |
| 8,815,889 B2 | 8/2014 | Cowley et al. |
| 8,916,195 B2 | 12/2014 | McKinney et al. |
| 8,969,371 B1 | 3/2015 | Klassen et al. |
| 9,107,837 B2 | 8/2015 | McKinney et al. |
| 9,119,850 B2 | 9/2015 | Klassen et al. |
| 9,125,868 B2 | 9/2015 | McKinney et al. |
| 9,248,123 B2 | 2/2016 | Dunayevich et al. |
| 9,457,005 B2 | 10/2016 | Cowley et al. |
| 9,633,575 B2 | 4/2017 | Klassen et al. |
| 2001/0025038 A1 | 9/2001 | Coffin et al. |
| 2001/0046964 A1 | 11/2001 | Percel et al. |
| 2002/0012680 A1 | 1/2002 | Patel et al. |
| 2002/0019364 A1 | 2/2002 | Renshaw |
| 2002/0022054 A1 | 2/2002 | Sawada et al. |
| 2002/0025972 A1 | 2/2002 | Hintz |
| 2002/0037836 A1 | 3/2002 | Henriksen |
| 2002/0044962 A1 | 4/2002 | Cherukuri et al. |
| 2002/0055512 A1 | 5/2002 | Marin et al. |
| 2002/0090615 A1 | 7/2002 | Rosen et al. |
| 2002/0132850 A1 | 9/2002 | Bartholomaeus et al. |
| 2002/0198227 A1 | 12/2002 | Bernstein |
| 2003/0003151 A1 | 1/2003 | Chopra |
| 2003/0017189 A1 | 1/2003 | Wong et al. |
| 2003/0035840 A1 | 2/2003 | Li et al. |
| 2003/0044462 A1 | 3/2003 | Subramanian et al. |
| 2003/0054031 A1 | 3/2003 | Li et al. |
| 2003/0054041 A1 | 3/2003 | Lemmens et al. |
| 2003/0055008 A1 | 3/2003 | Marcotte |
| 2003/0055038 A1 | 3/2003 | Howard et al. |
| 2003/0068371 A1 | 4/2003 | Oshlack et al. |
| 2003/0087896 A1 | 5/2003 | Glover |
| 2003/0091630 A1 | 5/2003 | Louie-Helm et al. |
| 2003/0109546 A1 | 6/2003 | Fenton |
| 2003/0130322 A1 | 7/2003 | Howard |
| 2003/0133982 A1 | 7/2003 | Heimlich et al. |
| 2003/0133985 A1 | 7/2003 | Louie-Helm et al. |
| 2003/0135056 A1 | 7/2003 | Anderson et al. |
| 2003/0144174 A1 | 7/2003 | Brenna et al. |
| 2003/0144271 A1 | 7/2003 | Shulman |
| 2003/0147952 A1 | 8/2003 | Lim et al. |
| 2003/0161874 A1 | 8/2003 | Li et al. |
| 2003/0198683 A1 | 10/2003 | Li et al. |
| 2003/0215496 A1 | 11/2003 | Patel et al. |
| 2004/0002462 A1 | 1/2004 | Najarian |
| 2004/0005368 A1 | 1/2004 | Mann et al. |
| 2004/0022852 A1 | 2/2004 | Chopra |
| 2004/0029941 A1 | 2/2004 | Jennings |
| 2004/0047908 A1 | 3/2004 | Lemmens et al. |
| 2004/0059241 A1 | 3/2004 | Suffin |
| 2004/0092504 A1 | 5/2004 | Benja-Athon |
| 2004/0096499 A1 | 5/2004 | Vaya et al. |
| 2004/0101556 A1 | 5/2004 | Li et al. |
| 2004/0105778 A1 | 6/2004 | Lee et al. |
| 2004/0106576 A1 | 6/2004 | Jerussi et al. |
| 2004/0115134 A1 | 6/2004 | Merisko-Liversidge |
| 2004/0122033 A1 | 6/2004 | Nargund et al. |
| 2004/0158194 A1 | 8/2004 | Wolff et al. |
| 2004/0185097 A1 | 9/2004 | Kannan et al. |
| 2004/0204472 A1 | 10/2004 | Briggs et al. |
| 2004/0228915 A1 | 11/2004 | Noack et al. |
| 2004/0228924 A1 | 11/2004 | Oshlack et al. |
| 2004/0242974 A1 | 12/2004 | Glover |
| 2004/0258757 A1 | 12/2004 | Bosch et al. |
| 2005/0004106 A1 | 1/2005 | Romano |
| 2005/0013863 A1 | 1/2005 | Lim et al. |
| 2005/0019385 A1 | 1/2005 | Houze |

(56) References Cited

U.S. PATENT DOCUMENTS

| | | |
|---|---|---|
| 2005/0019409 A1 | 1/2005 | Edgren et al. |
| 2005/0019412 A1 | 1/2005 | Bosch et al. |
| 2005/0026977 A1 | 2/2005 | Jennings |
| 2005/0026986 A1 | 2/2005 | Maruani et al. |
| 2005/0031691 A1 | 2/2005 | McGurk et al. |
| 2005/0043704 A1 | 2/2005 | Lieberburg |
| 2005/0043705 A1 | 2/2005 | Lieberburg |
| 2005/0043773 A1 | 2/2005 | Lieberburg |
| 2005/0063913 A1 | 3/2005 | Pruitt et al. |
| 2005/0096311 A1 | 5/2005 | Suffin et al. |
| 2005/0112198 A1 | 5/2005 | Challapalli et al. |
| 2005/0112211 A1 | 5/2005 | Gervais et al. |
| 2005/0118268 A1 | 6/2005 | Percel et al. |
| 2005/0137144 A1 | 6/2005 | Gadde et al. |
| 2005/0142195 A1 | 6/2005 | Li et al. |
| 2005/0143322 A1 | 6/2005 | Gadde et al. |
| 2005/0147664 A1 | 7/2005 | Liversidge et al. |
| 2005/0154002 A1 | 7/2005 | Crooks et al. |
| 2005/0163840 A1 | 7/2005 | Sawada et al. |
| 2005/0169990 A1 | 8/2005 | Kao et al. |
| 2005/0181049 A1 | 8/2005 | Dong et al. |
| 2005/0214368 A1 | 9/2005 | Kawakami et al. |
| 2005/0214371 A1 | 9/2005 | Di Capua et al. |
| 2005/0214372 A1 | 9/2005 | Di Capua et al. |
| 2005/0215552 A1 | 9/2005 | Gadde et al. |
| 2005/0232990 A1 | 10/2005 | Boehm et al. |
| 2005/0238718 A1 | 10/2005 | Oberegger et al. |
| 2005/0245460 A1 | 11/2005 | Meyerson et al. |
| 2005/0250838 A1 | 11/2005 | Challapalli et al. |
| 2005/0277579 A1 | 12/2005 | Gadde et al. |
| 2006/0009514 A1 | 1/2006 | Gadde et al. |
| 2006/0018933 A1 | 1/2006 | Vaya et al. |
| 2006/0018934 A1 | 1/2006 | Vaya et al. |
| 2006/0024365 A1 | 2/2006 | Vaya et al. |
| 2006/0051418 A1 | 3/2006 | Cowen et al. |
| 2006/0058293 A1 | 3/2006 | Weber et al. |
| 2006/0069086 A1 | 3/2006 | Michalow |
| 2006/0079501 A1 | 4/2006 | Gadde et al. |
| 2006/0100205 A1 | 5/2006 | Weber et al. |
| 2006/0122127 A1 | 6/2006 | Rao et al. |
| 2006/0160750 A1 | 7/2006 | Gadde et al. |
| 2006/0246131 A1 | 11/2006 | Cottinham |
| 2006/0276412 A1 | 12/2006 | Tollefson |
| 2007/0078135 A1 | 4/2007 | Yuan et al. |
| 2007/0099947 A1 | 5/2007 | Dean et al. |
| 2007/0117827 A1 | 5/2007 | Tollefson et al. |
| 2007/0129283 A1 | 6/2007 | McKinney et al. |
| 2007/0148237 A1 | 6/2007 | McKinney et al. |
| 2007/0149451 A1 | 6/2007 | Holmes |
| 2007/0179168 A1 | 8/2007 | Cowley et al. |
| 2007/0185084 A1 | 8/2007 | McKinney et al. |
| 2007/0270450 A1 | 11/2007 | Weber et al. |
| 2007/0275970 A1 | 11/2007 | Weber et al. |
| 2008/0027487 A1 | 1/2008 | Patel et al. |
| 2008/0058407 A1 | 3/2008 | Baron et al. |
| 2008/0110792 A1 | 5/2008 | McKinney et al. |
| 2008/0214592 A1 | 9/2008 | Cowley et al. |
| 2009/0018115 A1 | 1/2009 | Gadde et al. |
| 2009/0076108 A1 | 3/2009 | Gadde et al. |
| 2010/0166889 A1 | 7/2010 | Sanfilippo |
| 2010/0190793 A1 | 7/2010 | Weber et al. |
| 2011/0028505 A1 | 2/2011 | McKinney et al. |
| 2011/0098289 A1 | 4/2011 | Gadde et al. |
| 2011/0144145 A1 | 6/2011 | Tollefson |
| 2012/0010232 A1 | 1/2012 | Weber et al. |
| 2013/0177602 A1 | 7/2013 | McKinney et al. |
| 2013/0245056 A1 | 9/2013 | Flanagan |
| 2013/0252995 A1 | 9/2013 | Dunayevich et al. |
| 2014/0080857 A1 | 3/2014 | McKinney et al. |
| 2014/0364468 A1 | 12/2014 | Gadde et al. |
| 2015/0119417 A1 | 4/2015 | Tollefson |
| 2015/0164806 A1 | 6/2015 | McKinney et al. |
| 2015/0182524 A1 | 7/2015 | Klassen et al. |
| 2015/0366860 A1 | 12/2015 | Klassen et al. |
| 2016/0143903 A1 | 5/2016 | Dunayevich et al. |
| 2016/0158221 A1 | 6/2016 | McKinney et al. |
| 2016/0158225 A1 | 6/2016 | McKinney et al. |
| 2016/0193152 A1 | 7/2016 | McKinney et al. |
| 2016/0310485 A1 | 10/2016 | Klassen et al. |
| 2016/0338965 A1 | 11/2016 | McKinney et al. |
| 2016/0354348 A1 | 12/2016 | McKinney et al. |
| 2017/0014404 A1 | 1/2017 | McKinney et al. |
| 2017/0020990 A1 | 1/2017 | Cowley et al. |
| 2017/0172999 A1 | 6/2017 | Tollefson et al. |
| 2017/0221380 A1 | 8/2017 | Klassen et al. |
| 2017/0312269 A1 | 11/2017 | McKinney et al. |

FOREIGN PATENT DOCUMENTS

| | | |
|---|---|---|
| EP | 0 294 028 | 12/1988 |
| EP | 0 442 769 | 8/1991 |
| EP | 0 541 192 | 5/1993 |
| EP | 0 598 309 | 5/1994 |
| EP | 1 275 373 | 1/2003 |
| EP | 1 772 147 | 4/2007 |
| EP | 1 759 701 | 7/2007 |
| EP | 1 813 276 | 8/2007 |
| JP | 2003-502358 | 1/2003 |
| JP | 2003-509349 | 3/2003 |
| JP | 2006-232675 | 9/2006 |
| RU | 2197250 C2 | 1/2003 |
| RU | 2214241 | 10/2003 |
| RU | 2342195 C1 | 12/2008 |
| WO | WO 83/03197 | 9/1983 |
| WO | WO 90/13294 | 11/1990 |
| WO | WO 94/20100 | 9/1994 |
| WO | WO 96/09047 | 3/1996 |
| WO | WO 97/06786 | 2/1997 |
| WO | WO 97/06787 | 2/1997 |
| WO | WO 97/41873 | 11/1997 |
| WO | WO 98/00130 | 1/1998 |
| WO | WO 99/16375 | 4/1999 |
| WO | WO 99/37305 | 7/1999 |
| WO | WO 99/38504 | 8/1999 |
| WO | WO 00/050020 | 8/2000 |
| WO | WO 00/51546 | 9/2000 |
| WO | WO 00/61139 | 10/2000 |
| WO | WO 00/062757 | 10/2000 |
| WO | WO 00/76493 | 12/2000 |
| WO | WO 01/01973 | 1/2001 |
| WO | WO 01/26641 | 4/2001 |
| WO | WO 01/52833 | 7/2001 |
| WO | WO 01/52851 | 7/2001 |
| WO | WO 01/058447 | 8/2001 |
| WO | WO 01/58451 | 8/2001 |
| WO | WO 01/058451 | 8/2001 |
| WO | WO 01/62257 | 8/2001 |
| WO | WO 01/78725 | 10/2001 |
| WO | WO 01/85257 | 11/2001 |
| WO | WO 02/09694 | 2/2002 |
| WO | WO 02/24214 | 3/2002 |
| WO | WO 02/087590 | 11/2002 |
| WO | WO 03/013524 | 2/2003 |
| WO | WO 03/013525 | 2/2003 |
| WO | WO 03/013479 | 3/2003 |
| WO | WO 03/045355 | 6/2003 |
| WO | WO 03/092682 | 11/2003 |
| WO | WO 03/097051 | 11/2003 |
| WO | WO 04/002463 | 1/2004 |
| WO | WO 04/009015 | 1/2004 |
| WO | WO 04/024096 | 3/2004 |
| WO | WO 04/052289 | 6/2004 |
| WO | WO 04/054570 | 7/2004 |
| WO | WO 04/054571 | 7/2004 |
| WO | WO 04/060355 | 7/2004 |
| WO | WO 04/071423 | 8/2004 |
| WO | WO 04/091593 | 10/2004 |
| WO | WO 04/100956 | 11/2004 |
| WO | WO 04/100992 | 11/2004 |
| WO | WO 04/110368 | 12/2004 |
| WO | WO 04/110375 | 12/2004 |
| WO | WO 05/000217 | 1/2005 |
| WO | WO 05/077362 | 2/2005 |
| WO | WO 05/032555 | 4/2005 |

(56) References Cited

FOREIGN PATENT DOCUMENTS

| WO | WO 05/049043 | 6/2005 |
| WO | WO 05/079773 | 9/2005 |
| WO | WO 05/089486 | 9/2005 |
| WO | WO 06/049941 | 5/2006 |
| WO | WO 06/052542 | 5/2006 |
| WO | WO 06/055854 | 5/2006 |
| WO | WO 06/088748 | 8/2006 |
| WO | WO 07/012064 | 1/2007 |
| WO | WO 07/024700 | 3/2007 |
| WO | WO 07/047351 | 4/2007 |
| WO | WO 07/85637 | 8/2007 |
| WO | WO 08/119978 | 10/2008 |
| WO | WO 09/158114 | 12/2009 |
| WO | WO 11/119953 | 9/2011 |
| WO | WO 12/070043 | 5/2012 |
| WO | WO 13/184837 | 12/2013 |

OTHER PUBLICATIONS

Chilton et al., Oct. 2, 2011, Naltrexone SR/Bupropion SR combination therapy improves predicted 10-year risk of cardiovascular disease, coronary heart disease, myocardial infarction, and congestive heart failure, Obesity, 19(Suppl 1):S177.

Cleary et al., Jul. 1996, Naloxone effect on sucrose-motivated behavior, Psychopharmacology (Berl.), 126(2):110-114.

ClinicalTrials.gov, Dec. 20, 2006, Placebo-controlled trial of bupropion for the treatment of binge eating disorder, https://clinicaltrials.gov/ct2/show/study/NCT00414167, 3 pp.

Contrave (naltrexone HCI and bupropion HCI) extended-release tablets, initial U.S. approval, 2014.

Cusin et al., 2009, Chapter 2: Rating scales for depression, Handbook of Clinical Rating Scales and Assessment in Psychiatry and Mental Health, Baer et al., eds., Humana Press, pp. 7-35.

Fava, 2005, 15 years of clinical experience with bupropion HCI: from bupropion to bupropion SR to bupropion XL, Prim, Care Companion J. Clin Psychiatry, 7:106-113.

Minnaro et al., 1997, Aspectos technologicos de las formas farmaceuticas de liberacion modificada de administracion oral: sistemas matriciales, flotantes y bioadhesivos, Cienc. Pharm, 7(3):113-121.

O'Neil et al., Oct. 3, 2011, Naltrexone SR/Bupropion SR and intensive behavioral modification combination increases the likelihood of achieving early and sustained weight loss and associated improvement in markers of cardiometabolic risk, Obesity, 19(Suppl 1):S179-S180.

Padwal et al., Oct. 2009, Contrave, a bupropion and naltrexone combination therapy for the potential treatment of obesity, Current Opinion in Investigational Drugs, 10:1117-1125.

Remington: The Science and Practice of Pharmacy, 20th Ed., Chapter 45: Oral Solid Dosage Forms, pp. 858-893, 2003.

Shikh, Jan. 27, 2007, Bioavailability of oral medications, Russian Medical Journal, 2:95.

Sneer et al., 1979, Revista medico-chirurgicala, 83(1):87-91.

Thorndike, Jan. 28, 2008, Depressive symptoms and smoking cessation after hospitalization for cardiovascular disease, Arch Intern Med, 168(2):186-191.

Wikipedia, Major depressive disorder, downloaded on Oct. 9, 2017 from en.wikipedia.org.wiki/Major_depressive_disorder, 1 p.

www.1000mealplans.com (accessed Feb. 21, 2017), 2 pp.

Ackerman et al., 1998, Clinical characteristics of response to fluoxetine treatment of obsessive-compulsive disorder. Journal of Clinical Psychopharmacology, 18(3):185-192.

Adis Data Information BV, 2010, Naltrexone/Bupropion Contrave®; Naltrexone SR/Bupropion SR, Adis R&D Profile, 10(1):25-32.

Albaugh et al., 2005, Topiramate prevents the rapid weight gain and adiposity in a model of atypical antipsychotic drug-induced obesity, Fed. of American Soc. For Experimental Biology, 19(5, Suppl. S, Part 2):A1130.

Alger et al., Apr. 1991, Effect of a tricyclic antidepressant and opiate antagonist on binge-eating behavior in normoweight bulimic and obese, binge-eating subjects, The American Journal of Clinical Nutrition, 53(4):865-871.

Altman et al., 2005, Standard Deviations and Standard Errors, BMJ, 331:903.

Anderson et al., 2002, Bupropion SR enhances weight loss: a 48-week double-blind, placebo-controlled trial, Obesity R., 10(7):633-641.

Appolinario et al., 2004, Pharmacological Approaches in the Treatment of Binge Eating Disorder, Current Drug Targets, 5:301-307.

Aronne et al., 2003, Weight gain in the treatment of mood disorders, J. Clin Psychiatry, 64(suppl 8).

Asconape, 2002, Some Common Issues in the Use of Antiepileptic Drugs, Seminars in Neurology; 22(1):27-39.

Astrup et al., Mar. 1991, Thermogenic Synergism Between Ephedrine and Caffeine in Healthy Volunteers: A Double-Blind, Placebo-Controlled Study, Metabolism, 40(3):323-329.

Atkinson et al. (Oct. 1985) Effects of long-term therapy with naltrexone on body weight in obesity, Clinical Pharmacology & Therapeutics, 38:419-422.

Atkinson, 2003, Clinical Guidelines on the identification, Evaluation, and pharmacologic treatment of obesity in Adults, Online, 07-25, URL:http://www.endotext.org.obesity/obesity15b/obesity15b.htm.

Atlantis et al., Oct. 6, 2009, Obesity and depression or anxiety, BMJ 2009:339:B3868.

Ayala (2000) Weight Loss Associated With the Administration of Zonisamide, AES Proceedings, Epilepsia 41(Suppl. 7) :99—No. 2.041.

Ayala et al., Dec. 1-6, 2000, Weight loss associated with the administration of zonisamide, a compendium of posters and platform session for ZonegranTM and Diastat®, Annual Meeting 2000 of the American Epilepsy Society, Los Angeles, CA.

Baldassano et al. (2006) Acute treatment of bipolar depression with adjunctive zonisamide: a retrospective chart review, Disorders 6:432-434.

Barr et al. 1993. The serotonin hypothesis of obsessive compulsive disorder. International Clinical Psychopharmacology, 8(2):79-82.

Bastani et al. 1991. Serotonin uptake and imipramine binding in the blood platelets of obsessive-compulsive disorder patients. Biol. Psychiatry, 30:131-139.

Bays et al., Aug. 1, 2007, Adiposopathy: treating pathogenic adipose tissue to reduce cardiovascular disease risk, Current Treatment Options in Cardiovascular Medicine, 9(4):259-271.

Beelen et al. (2001) Asymptomatic QTC prolongation associated with queitiapine fumarate overdose in a patient being treated with risperidone, Human & Experimental Toxicology 20:215-219.

Benjamin et al. 1993. Naltrexone and fluoxetine in Prader-Willi syndrome. J. Am. Acad. Child Adolesc. Psychiatry, 32(4):870-873.

Bergeron et al. 2002. Sertraline and fluoxetine treatment of obsessive-compulsive disorder: Results of a double-blind, 6-month treatment study. Journal of Clinical Psychopharmacology, 22(2):148-154.

Berke et al. (Jul. 15, 2000) Medical Management of Obesity, American Academy of Family Physicians, 62(2):419-26 Abstract.

Billett et al. 1997. Obsessive compulsive disorder, response to serotonin reuptake inhibitors and the serotonin transporter gene. Molecular Psychiatry, 2:403-406.

Blanchard et al. (2003) Pancreatitis Treated with Didanosine and Tenofabir Disoproxil Fumarate Clinical Infectious Diseases, 37:57-62.

Broocks et al. 1998. Higher prevalence of obsessive-compulsive symptoms in patients with blepharospasm than in patients with hemifacial spasm. Am. J. Psychiatry, 155:555-557.

Bupropion (Oral Route), MayoClinic.com, 19 pp., 2009.

Calabrese et al. (Sep. 2000) Letters to the Editors, Lamotrigine and Clozapine for Bipolar Disorder, American J. of Psychiatry, 157:1523.

Campana et al., Jan. 2005, P.6.034 Naltrexone and cravings: does it work with eating disorders?, European Neuropsychopharmacology, 15:S283.

Carlsen et al. (Jan. 1998) Evidence for dissociation of insulin- and weight-reducing effects of metformin in non-diabetic male patients with coronary heart disease, Diabetes Research and Clinical Practice Amersterdam, 39(1):47-54.

Carpenter et al. (Jan. 1, 1999) Mirtazapine Augmentation in the Treatment of Refractory Depression, J Clin Psychiatry, 60:1.

(56) References Cited

OTHER PUBLICATIONS

Carrion, 1995. Naltrexone for the treatment of trichotillomania: A case report. J. Clin. Psychopharmacol., 15(6):444-445.
Carroll (2003) Medicinal Chemistry Division Award Address: Monoamine Transporters and Opioid Receptors. Targets for Addiction Therapy, J. Med. Chem; 46(10):1775-1794.
Carter et al. 2003. Pharmacologic treatment of binge-eating disorder, The International Journal of Eating Disorders, 34(Suppl):S74-S88.
Carter et al. 2003. Pharmacologic treatment of binge-eating disorder. Primary Psychiatry, 10(10)31-36.
Casado et al., Apr. 2003, Sibutramine decreases body weight gain and increases energy expenditure in obese Zucker rats without changes in NPY and orexins, Nutr Neurosci, 6(2):103-111 (abstract).
Cash et al. (2000) Attitudes about antidepressants: Influence of information about weight-related side effects, Perceptual and Motor Skills, 90:453-456.
Casner et al. 1996. Naltrexone and self-injurious behavior: A retrospective population study. Journal of Clinical Psychopharmacology, 16(5):389-394.
Chen et al. (Jan. 2004) Synergistic Effects of Cannabinoid inverse agonist AM251 and opioid antagonist nalmefene on food intake, Brain Res, 999:22-230.
Chen et al., 2005, Combination treatment of clozapine and (No Suggestions) in resistant rapid-cycling bipolar disorder, Clin. Neuropharmacol. 28(3):136-138.
Chen et al., Jun. 2003, Nonketotic hyperosmolar syndrome from olanzapine, lithium, and valproic acid cotreatment, Annals of Pharmacotherapy, 37(6):919-920.
Chengappa et al. (2002) Changes in body Weight and Body mass index among psychiatric patients receiving lithium, valproate, or topiramate: an open-label, nonrandomized chart review, Clinical Therapeutics, 24(10):1576-1584.
Ching, Mar. 1980, Influence of diphenylhydantoin upon oral glucose tolerance test in obesity, Chinese Medical Journal, 27(1):432-439.
Chouinard et al. 1996. Potentiation of fluoxetine by aminoglutethimide, an adrenal steroid suppressant, in obsessive-compulsive disorder resistant to SSRIs: A case report. Prog. Neuro-Psychopharmacol. & Biol. Psychiat., 20:1067-1079.
Clapham et al. (2001) Anti-obesity drugs: a critical review of current therapies and future opportunities. Pharmacology & Therapeutics. 89:81-121.
Clark et al., 2003, Diabetes mellitus associated with atypical antipsychotic medications, Diabetes Technology & Therapeutics, 5(4):669-683.
Clinical Trial: Drug Treatment for Depressed Alcoholics (Naltrexone/Fluoxetine). (n.d.) Retrieved Jun. 28, 2007, from http://www.clinicaltrials.gov/ct/show/NCT00006204;jsessionid+FED6D0856E098BC0B1940E464179B71B?order=28.
ClinicalTrials.gov archive, Apr. 21, 2008, A phase 3 study comparing the safety and efficacy of naltrexone sr/bupropion sr and placebo in obese subjects with type 2 diabetes mellitus, 3 pp.
ClinicalTrials.gov archive, May 2012, Cardiovascular outcomes study of Naltrexone SR/Bupropion SR in overweight and obese subjects with cardiovascular risk factors (the light study), 4 pp.
Colosimo, et al. 1999. Motor fluctuations in Parkinson's disease: Pathophysiology and treatment. European Journal of Neurology, 6:1-21.
Cone et al. (2001) The arcuate nucleus as a conduit for diverse signals relevant to energy homeostasis, Int'l Journal of Obesity, 25(5):S63-S67.
Croft et al. (Apr. 2002) Effect on body weight of bupropion sustained-release in patients with major depression treated for 52 weeks, Clinical Therapeutics 24(4):662-672.
Cunningham, May 1963, Diethylpropion in the treatment of obesity, The Journal of the College of General Practitioner, 6(2):347-349.
Cuparencu et al., 1993, Effects of some benzodiazepines on glycemia in albino rats, Romanian Journal of Physiology, 30(1-2):7-15 (abstract).

Dechant et al., 1991, Paroxetine: a review of its pharmacodynamic and pharmacokinetic properties, and therapeutic potential in depressive illness, Drugs, 41:225-253.
Dembowski et al. (2003) Successful Antimanic Treatment and Mood Stabilization with Lamotrigine, Clozapine, and Valproate in a Bipolar Patient after Lithium-induced Cerebellar Deterioration, Letter Pharmacopsychiatry, 36:83-86.
Deshmukh et al. (Jul. 2003) Managing weight gain as a side effect of antidepressant therapy, Cleveland Clinic Journal of Medicine, 70(7):614-623.
DeSimone et al. (2005) Carbonic anhydrase inhibitors. Zonisamide is an effective inhibitor of the cytosolic isozyme II and mitochondrial isozyme V: Solution and x-ray crystallographic studies, Bioorganic & Medicinal Chemistry Letters, 15:2315-2320.
Devlin et al. (2000) Open treatment of overweight binge eaters with phentermine and fluoxetine as an adjunct to cognitive-behavioral therapy. Int. J. Eating Disord; 28:325-332.
Durgin et al., 2005, Pharmaceutical Practice for Technicians, 3rd Edition, Thomson Delmar Learning, p. 174.
Dursun et al. (2001) Accelerated Weight Loss After Treating Refractory Depression with Fluoxetine Plus Topiramate: Possible Mechanism of Action, Canadian Journal of Psychiatry, 46(3):287-288.
Dursun et al. (2001) Augmenting Antipsychotic treatment with Lamotrigine or topiramate in patients with treatment-resistant Schizophrenia: a naturalistic case-series outcome study Journal of Psychopharmacology 15(4):297-301.
Dursun et al. (2001) Psychopharmacology for the Clinician Psychopharmacologie Pratiqu, Journal of Psychiatry Neuroscience, 26(2):168.
Dursun et al. (Oct. 1999) Clozapine Plus Lamotrigine in Treatment-Resistant Schizophrenia, Arch Gen Psychiatry, 56:950-951.
Dwyer et al., 2002, Psychoactive drugs affect glucose transport and the regulation of glucose metabolism, International Review of Neurobiology, 51:503-530.
El-Haschimi et al. 2000. Two defects contribute to hypothalamic leptin resistance in mice with diet-induced obesity. The Journal of Clinical Investigation, 105(12):1827-1832.
Erez et al., 1982, Narcotic antagonistic potency of bivalent ligands which contain ß-naltrexamine. Evidence for bridging between proximal recognition sites, J. Med. Chem., 25:847-849.
Erfurth et al., Mar. 2002, Bupropion as add-on strategy in difficult-to-treat bipolar depressive patients, Neurophsychobiology, 45(Supplement 1):33-36.
Erzegovesi et al. 2001. Clinical predictors of drug response in obsessive-compulsive disorder. Journal of Clinical Psychopharmacology, 21(5):488-492.
Esposito-Avella et al. (Jan. 1973) Studies on the protective effect of diphenylhyndantoin against alioxan diabetes in mice, Proceedings of the Society for Experimental Biology & Medicine, 142(1):82-85.
Ettmayer et al, May 6, 2004, Lessons learned from marketed and investigational prodrugs, J. Med. Chem, 47(10):2393-2404.
Faught et al. (2001) Randomized Controlled Trial of Zonisamide for the Treatment of Refractory Partial-Onset Seizures., Neurology; 57(10):1774-1779.
Fava, 2000, Weight Gain and Antidepressants. J Clin Psychiatry; 61(suppl 11):37-41.
Ferre et al. (1996) Correction of diabetic alterations by glucokinase. Proc. Natl. Acad. Sci. USA, 93:7225-7230.
Ferre et al. (1996) Evidence from transgenic mice that glucokinase is rate limiting for glucose utilization in the liver, The FASEB Journal, 10:1213-1218.
Fingl et al., The Pharmacological Basis of Therapeutics. Chapter 1: General Principles, pp. 1-46 (1975).
Fontela et al., Mar. 1986, Blocking effect of naloxone, dihydroergotamine and adrenalectomy in lithium-induced hyperglycaemia and glucose intolerance in the rat, Acta Endocrinologica, 111(3):342-348 (abstract).
Fujioka et al., Jan. 1987, Contribution of intra-abdominal fat accumulation to the impairment of glucose and lipid metabolism in human obesity, Metabolism, 36(1):54-59.
Fukagawa et al. (Nov. 2001) Monoaminergic anorectic agents, Nippon Yikurigaku Zasshi, 118(5):303-8, 2001 Abstract.

(56) References Cited

OTHER PUBLICATIONS

Fulghesu et al. (Aug. 1993) Long-term naltrexone treatment reduces the exaggerated insulin secretion in patients with polycystic ovary disease, Obstetrics & Gynecology, 82(2):191-197.
Fuller et al. (1989) Fluoxetine: A Serotonergic Appetite Suppressant Drug, Drug Development Research, 17(1):1-15.
Gadde et al, "Zonisamide in Obesity: A 16-Week Randomized Trial", No. NR473, New Research, American Psychiatric Association 2002 Annual Meeting, May 18-23, 2002, Philadelphia, Pennsylvania (abstract).
Gadde et al, Randomized Trial of Weight Loss Efficacy of Zonisamide, No. 304, 26(Suppl. 1), Journal of the International Association for the Study of Obesity, Ninth International Congress on Obesity, Sao Paolo, Brazil, Aug. 24-29, 2002.
Gadde et al. "Bupropion for Weight Loss: An Investigation of Efficacy and Tolerability in Overweight and Obese Women" Obesity Research 9 (9): 544-551 (2001).
Gadde et al., "Zonisamide for Weight Loss in Obese Adults—A Randomized Controlled Trial" JAMA 289 (14): 1820-1825 (2003).
Gadde et al., 2002, Randomized controlled trial of zonisamide for treating obesity, Epilepsia 43 Suppl. 7:218 (abstract).
Gadde et al., 2003, Zonisamide enhances weight loss in patients with obesity. Inpharma, 1383(84):9.
Gadde et al., May 1999, Bupropion Sustained Release in Obesity: A Randomized Double-Blind, Placebo-Controlled Study, No. NR634, New Research Program & Abstracts, American Psychiatric Association, 1999 Annual Meeting, The Clinician, Washington, D.C.
Gadde et al., Sep. 1999, A randomized double-blind placebo-controlled study of bupropion sustained release in obesity, European Neuropsychopharmacology, 9(5):366.
Gatley et al., 1996, 123I-labeled AM251: a radioiodinated ligand which binds in vivo to mouse brain cannabinoid CB1 receptors. European Journal of Pharmacology; 307:331-338.
Gehlert et al. (Oct. 1998) The Selective Norepinephrine Reuptake Inhibitor, LY368975, Reduces Food Consumption in Animal Models of Feeding, J. Pharmacology and Experimental Therapeutics, 87(1):122-7 Abstract.
Gerich et al. (1972) In vitro inhibition of pancreative glucagon secretion by diphenylhydantoin, Journal of Clinical Endocrinology and Metabolism 35(6):823-824.
Gerra et al. 1995. Hostility in heroin abusers subtypes: Fluoxetine and naltrexone treatment. Prog. Neuro-Psychopharmacol. & Biol. Psychiat., 19:1225-1237.
Gerra et al., Sep. 30, 2006, Effects of olanzapine on aggressiveness in heroin dependent patients, Progress in Neuro-Psychopharmacology & Biological Psychiatry, 30(7):1291-1298.
Ginsberg et al. (2000) Effects of Mood Stabilizers on Weight, Primary Psychiatry 7(5):49-58.
Givens et al. (1987) Reduction of hyperinsulinemia and insulin resistance by opiate receptor blockade in the polycystic ovary syndrome with acanthosis nigricans, Journal of Clinical Endocrinology and Metabolism, 64(2):377-382.
Glass et al., 1999, Opioids and food intake: distributed functional neural pathways?, Neuropeptides, 33(5):360-368.
Goldstein et al. (Mar. 1994) Fluoxetine: a randomized clinical trial in the treatment of obesity, International Journal of Obesity and Related Metabolic Disorders, 17(3):129-135, CAS accession #9424430.
Goodman et al. 1989. The Yale-Brown obsessive compulsive scale. Arch. Gen. Psychiatry, 46:1006-1011.
Gordon et al. (Jun. 1999) Mood Stabilization and Weight Loss with Topiramate American Journal of Psychiatry, American Psychiatric Association, Washington D.C., 156(6):968-969.
Gormally et al., 1982, The assessment of binge eating severity among obese persons, Addict Behav, 7(1):47-55.
Grady (Mar. 15, 2003) Quest for Weight-Loss Drug Takes an Unusual Turn, The New York Times—Health, www.nytimes.com, 3 pp.
Grant et al. 2004. Impulse control disorders: Clinical characteristics and pharmacological management. Annals of Clinical Psychiatry, 16:27-34.
Grant et al. 2004. Pharmacotherapy outcome in older pathological gamblers: A preliminary investigation. Journal of Geriatric Psychiatry and Neurology, 17(1):9-12.
Grant et al. 2006. Compulsive aspects of impulse-control disorders. Psychiatr. Clin. North Am., 29(2):539-x.
Greenberg et al. 1998. Delayed obsessive-compulsive disorder symptom exacerbation after a single dose of a serotonin antagonist in fluoxetine-treated but not untreated patients. Psychopharmacology, 140:434-444.
Greenway et al. (2002) A Long-acting Leptin Analog does not Enhance Fat, Visceral Fat, or Weight Loss When Combined with Caffeine Ephedrine in Obese Subjects, International Journal of Obesity, S136.
Greenway et al. (Jul. 1999) Double-Blind, Randomized, Placebo-Controlled Clinical Trials with Non-prescription Medications for the Treatment of Obesity, Obesity Research, 7(4):370-78.
Greenway et al., Dec. 2009, Comparison of combined bupropion and naltrexone therapy for obesity with monotherapy and placebo, J. Clin Endocrinol Metab, 94(12):4898-4906.
Greenway et al., Jan. 2009, Rational design of a combination medication for the treatment of obesity, Obesity, 17(1):30-39.
Greenway et al., Jun. 2006, Bupropion and naltrexone for the treatment of obesity, Diabetes: Abstract Book: 66th Scientific Sessions, 55(Supplement 1):A395.
Greenway et al., Jun. 2006, Bupropion and naltrexone for the treatment of obesity, poster, 1 pg.
Greenway et al., Oct. 22, 2010, Effect of naltrexone plus bupropion on weight loss in overweight and obese adults (COR-I): a multicentre, randomized, double-blind, placebo-controlled, phase 3 trial, Lancet, 376:595-605.
Greist et al. (Apr. 1995) Double-blind Parallel Comparison of Three Dosages of Sertraline and Placebo in Outpatients With Obsessive-compulsive Disorder, Arch Gen Psychiatry, 52:289-295.
Grunenthal, Neo-Eunomin Gebrauchsinformation, Neunomin Prescription Information, Feb. 2004, pp. 1-2.
Hagan et al., Dec. 1997, Combined naloxone and fluoxetine on deprivation-induced binge eating of palatable foods in rats, Pharmacol Biochem Behav, 58(4):1103-1107.
Hahn et al. (1985) Irreversible opiate agonists and antagonists. III. Phenylhydrazone derivatives of naloxone and oxymorphone. J. Pharm. Exper. Therapeutics; 235:846-850.
Halpern et al., Jul. 27, 2010, Combinations of drugs in the treatment of obesity, Pharmaceuticals, 3:2398-2415.
Hamidi et al. 2007. Naltrexone in obsessive-compulsive disorder: An open-label trial. Iranian Journal of Psychiatry and Behavioral Sciences, 1(1):16-21.
Harrison's Principles of Internal Medicine, Braunwald et al., The epilepsies and convulsive disorders, Eleventh Edition, McGraw-Hill Book Company, pp. 1921-1930 (1987).
Hashiguti et al. (1993) Simultaneous determination of in vivo hydroxylation of tyrosine and tryptophan in rat striatum by microdialysis—HPLC: relationship between dopamine and serotonin biosynthesis; Journal of Neural Transmission, 93:213-223.
Hausenloy, 2009, Contrave™: Novel treatment for obesity, Clinical Lipidology, 4(3):279-285.
Hollander et al. 1991. Effects of chronic fluoxetine treatment on behavioral and neuroendocrine responses to meta-chlorophenylpiperazine in obsessive-compulsive disorder. Psychiatry Research, 36:1-17.
Horne et al., Jul. 1988, Treatment of bulimia with bupropion: a multicenter controlled trial, The Journal of Clinical Psychiatry, 49(7):262-266.
Hussey et al., 2002, Synthesis of a ß-estradiol-biotin chimera that potently heterodimerizes estrogen receptor and streptavidin proteins in a yeast three-hybrid system, J. Am. Chem. Soc., 125:3692-3693.
Insulin Resistance and Pre-diabetes, http://diabetes.niddk.hih.gov/DM/pubs/insulineresistance/, NIH Publication No. 09/4893, Oct. 2008, 9 pp.
Islam et al., 1994, Naltrexone, Serotonin Receptor Subtype Antagonists, and Carbohydrate Intake in Rats, Pharmacology Biochemistry and Behavior, 48(1):193-201.

(56) References Cited

OTHER PUBLICATIONS

Jain et al. (Oct. 2002) Bupropion SR vs. Placebo for Weight Loss in Obese Patients with Depressive Symptoms, Obesity Research, 10:1049-56.
Jallon et al. (2001) Bodyweight gain and anticonvulsants: a comparative review. Drug Safety; 24(13):969-978.
Janssen et al., 1999, Effects of sex on the change in visceral, subcutaneous adipose tissue and skeletal muscle in response to weight loss, International Journal of Obesity, 23, pp. 1035-1046.
Japanese Journal of Clinical Psychiatry (1987 16(1):123-132), and English-language version of Japanese Office Action citing the same (dated Oct. 28, 2008).
Johnson et al., Oct. 14, 2010, Food effects on the pharmacokinetics of morphine sulfate and naltrexone hydrochloride extended release capsules, Advances in Therapy, 27(11):846-858.
Jonas et al.., 1986, Treatment of binge-eating an open-study of naltrexone, Society for Neuroscience Abstracts, 12(1):595.
Jones et al., 2003, Effect of naltrexone on food intake and body weight in Syrian hamsters depends on metabolic status, Physiology & Behavior 28:67-72.
Kanba et al. (1994) The first open study of zonisamide, a novel anticonvulsant, shows efficacy in mania. Progress in Neuro-Psychopharmacology and Biological Psychiatry; 18(4):707-715.
Kelly et al., 2006, Adjunct divalproex or lithium to clozapine in treatment-resistant schizophrenia, Psychiatric Quarterly, 77(1):81-94.
Kennett et al., Nov. 2010, New approaches to the pharmacological treatment of obesity: can they break through the efficacy barrier?, Pharmacology Biochemistry and Behavior, 97(1):63-83.
Khaylis et al., Nov. 2010, A review of efficacious technology-based weight-loss interventions: five key components, Telemedicine and e-Health, 16(9):931-938.
Kim et al. 1990. Open fixed dose trial of fluoxetine in the treatment of obsessive compulsive disorder. Drug Development Research, 19:315-319.
Kimura et al., 1992, Pharmacokinetic interaction of zonisamide in rats: effects of other antiepileptics on zonisamide, J. Pharmacobio-Dyn. 15:631-639.
Kiptoo et al. (2006) Enhancement of Transdermal delivery or 6-B-naltrexol via a codrug linked to hydroxybupropion, Journal of Controlled Release 113:137-145.
Kirkham et al. (2001) Synergistic effects of opioid and cannabinoid antagonists on food intake. Psychopharmacology; 153:267-270.
Kirov et al. (2003) Add-on topiramate reduces weight in overweight patients with affective disorders: a clinical case. BMC Psychiatry, 5:19, 8 pp.
Kivimaki et al., Common mental disorder and obesity—insight from four repeat measures over 19 years: prospective Whitehall II cohort study, BMJ 2009; 339:b3765.
Klok et al., 2002, Cholesteryl-(I-lactic acid)n building blocks for self-assembling biomaterials, Macromolecules, 35:746-759.
Kolb et al. (1985) Synthesis and Pharmacological Characterization of Fluorescent Opioid Receptor Probes. A. Pharmaceutical Res, 2(6):266-271.
Korner et al. (2003) The emerging science of body weight regulation and its impact on obesity treatment, J. Clin. Invest. 111(5):565-570.
Kossard, et al. 2006. Defining urticarial dermatitis: A subset of dermal hypersensitivity reaction pattern. Arch. Dermatol., 142:29-34.
Krauss et al. 1997. Tics secondary to craniocerebral trauma, Movement Disorders, 12(5):776-782.
Kristeller et al., Jan. 12, 1999, An exploratory study of a meditation-based intervention for binge eating disorder, J. Health Psychol, 4(3):357-363.
Krupitsky et al. 2006. Naltrexone with or without fluoxetine for preventing relapse to heroin addiction in St. Petersburg, Russia. Journal of Substance Abuse Treatment, 31:319-328.
Kuk et al., 2006, Visceral fat is an independent predictor of all-cause mortality in men, Obesity, 14(2):336-341.

Kushner et al. (Mar. 2002) Obesity pharmacology: past, present, and future, Current Opinion in Gastroenterology, pp. 213-220.
Landabaso et al. 1998. A randomized trial of adding fluoxetine to a naltrexone treatment programme for heroin addicts. Addiction, 93(5):739-744.
Le Bourdonnec et al., 2002, Reporter affinity labels: an o-phthalaldehyde derivative of β-naltrexamine as a fluorogenic ligand for opioid receptors, J. Med. Chem., 43(13):2489-2492.
Leppik (Dec. 2004) Zonisamide: chemistry, mechanism of action, and pharmacokinetics, Seizure, 13(Suppl 1):S5-9; discussion S10.
Leppik et al. (1993) Efficacy and safety of zonisamide: results of a multicenter study. Epilepsy Research; 14:165-173.
Lesch et al. 1991. Long-term fluoxetine treatment decreases 5-HT1A receptor responsivity in obsessive-compulsive disorder. Psychopharmacology, 105:415-420.
Lessig et al. (Dec. 2001) Topiramate for Reversing Atypical Antipsychotic Weight Gain, J. Am. Child Adolesc. Psychiatry 40(12):1364.
Levy et al. (Nov. 2002) Topiramate Produced Weight Loss Following Olanzapine-Induced Weight Gain in Schizophrenia, J. Clin. Psychiatry, 63(11):1045.
Levy et al. 1985. Utility of free level monitoring of antiepileptic drugs. Epilepsia, 26(3):199-205.
Lin et al. 2000. Development of high fat diet-induced obesity and leptin resistance in C57B1/6J mice. International Journal of Obesity, 24:639-646.
López-Ibor, Jr. et al. 1996. Double-blind comparison of fluoxetine versus clomipramine in the treatment of obsessive compulsive disorder. European Neuropsychopharmacology, 6:111-118.
Lowry, Feb. 2008, Study: bupropion-naltrexone combo best for weight loss, Clinical Psychiatric News, 1 pp.
Luppino et al., Mar. 2010, Overweight, obesity, and depression: a systematic review and meta-analysis of longitudinal studies, Arch Gen Psychiatry, 67(3):220-229.
Malcolm et al. (Jun. 1985) A Controlled Trial of Naltrexone in Obese Humans, International Journal of Obesity, 9:347-353.
Malhotra et al. (2002) Medical Management of Obesity Associated With Mental Disorders, Journal of Clinical Psychiatry, 63(suppl 4):24-32.
Marrazzi et al., Feb. 1995, Binge eating disorder: response to naltrexone, International Journal of Obesity, 19(2):143-145.
Matsuura (2000) Indication for Anterior Temporal Lobectomy in Patients with Temporal Lobe Epilepsy and Psychopathology, Epilepsia, 41(Suppl. 9):39-42.
McDougle et al. (Aug. 2000) A double-blind, placebo-controlled study of risperidone addition in serotonin reuptake inhibitor-refractory obsessive-compulsive disorder, Archive of General Psychiatry, 57(8):794-801.
McElroy et al. (2000) Pharmacologic agents for the treatment of acute bipolar mania, Biological Psychiatry, 48(6):539-557.
McElroy et al. (2004) Zonisamide in the Treatment of Binge-Eating Disorder: An Open-Label, Prospective Trial, J. Clin. Psychiatry, 65(1):50-56.
McElroy et al. (2004) Zonisamide is effective in the treatment of binge-eating disorder. Inpharma; 1428:10.
McLaughlin et al. (2003) The cannabinoid CB1 antagonists SR 141716A and AM 251 suppress food intake and food-reinforced behavior in a variety of tasks in rats. Behavioral Pharmacology; 14:583:588.
McLaughlin et al., 1983, Nalmefene decreases meal size, food and water intake and weight gain in Zucker rats, Pharmacology Biochemistry and Behavior, 19(2):235-240 (abstract).
Meyer, Dec. 2008, Alleviation of both binge eating and sexual dysfunction with naltrexone, Journal of Clinical Psychopharmacology, 28(6):722-723.
Michelson et al. (Nov. 2001) Atomexetine in the Treatment of Children and Adolescents with Attention Deficit/Hyperactivity Disorder: A Randomized, Placebo-Controlled, Dose-Response Study, Pediatrics,108(5):E83 Abstract.
Midha et al., May 2005, Exposure measures applied to the bioequivalence of two sustained release formulations of bupropion, International Journal of Clinical Pharmacology and Therapeutics, 43(5):244-254.

(56) References Cited

OTHER PUBLICATIONS

Millet et al. 1999. Obsessive-compulsive disorder: Evaluation of clinical and biological circadian parameters during fluoxetine treatment. Psychopharmacology, 146:268-274.
Mitchell et al. (1987) High-Dose Naltrexone Therapy and Dietary Counseling for Obesity, Biological Psychiatry, 22:35-42.
Monteleone et al. 1995. Plasma melatonin and cortisol circadian patterns in patients with obsessive-compulsive disorder before and after fluoxetine treatment. Psychoneuroendocrinology, 20(7):763-770.
Morris, III (Dec. 3, 2000) The Effect of Zonisamide Administration on Patient Weight, A Scientific Exhibit at the American Epilepsy Society Annual Meeting, Los Angeles, California.
Must et al. (Oct. 27, 1999) The disease burden associated with overweight and obesity, JAMA, 282(16):1523-1529.
Najim et al., Dec. 1, 1993, Role of endorphins in benzodiazepine-induced hyperglycaemia in mice, Pharmacology Biochemistry and Behavior, 46(4):995-997.
Naltrexone (Oral Route), MayoClinic.com, 11 pp., 2009.
Nash et al., Jul. 1, 2004, Anxiety disorders, Medicine, 32(7):17-21.
National Institutes of Health, Apr. 18, 2008, Efficacy and safety study of combination therapy to treat uncomplicated obesity, http://clinicaltrials.gov/show/NCT00364871, 5 pp.
Navarro et al. (Jun. 2001) Topiramate for Clozapine-Induced Seizures, Am. J. Psychiatry, 158(6):968-969.
NDA 20-711, Approval Letter of Application No. NDA 20-711, Department of Health and Human Services, May 14, 1997, 4 pp.
NDA 20-789/S-005 ZONEGRAN (zonisamide) Capsules 100 mg, FDA Approved Labeling Text dated Oct. 7, 2002, 2 pp.
NDA20-789, ZONEGRAN (zonisamide) Capsules 100 mg, FDA Approved Labeling Text, p. 1-24 (Mar. 27, 2000).
Neumeister et al. 1999. Addition of naltrexone to fluoxetine in the treatment of binge eating disorder. Am. J. Psychiatry, 156(5):797.
NIH Publication No. 05-3892, Dec. 2004, National Diabetes Statistics, 18 pp.
Ninan et al., 1992, An improved synthesis of noroxymorphont, Tetrahedron., 48(32):6709-6716.
Niswender et al. 1997. Effects of increased glucokinase gene copy number on glucose homeostatis and hepatic glucose metabolism. The Journal of Biological Chemistry, 272(36):22570-22575.
Note for guidance on stability testing of existing active substances and related finished product, Committee for Proprietary Medicinal Products (CPMP), Apr. 22, 1998, 9 pp.
Novi et al. (Apr.-Jun. 1990) The role of opioid antagonists in the treatment of obesity. Results of a clinical trial with naltrexone, Minerva Endocrinol. 15(2):121-123, Abstract.
O'Byrne et al., Jan. 1, 1990, Effects of drugs on glucose tolerance in non-insulin-dependent diabetes (part II), Drugs, Adis International Ltd., 40(2):204-219.
Okada et al. (1992) Effects of zonisamide on extracellular levels of monoamine and its metabolite, and on Ca2+ dependent dopamine release Epilepsy Research, 13:113-119.
Okada et al. (1995) Effects of zonisamide on dopaminergic system, Epilepsy Research, 22:198-205.
Olsen et al., (1990) Conjugate Addition Ligands of Opioid Antagonists. Methacrylate Esters and Ethers of 6Alpha- and 6Beta-Naltrexol, Journal of Medicinal Chemistry, American Chemical Society, 33(2):737-741.
Olszewski et al. (Jun. 13, 2001) Evidence of Interactions Between Melanocortin and Opioid Systems in Regulation of Feeding, NeuroReport, 12(8):1727-1730.
Oommen et al. (1999) Zonisamide: A new antiepileptic drug. Clinical Neuropharmacology, 22(4):192-200.
Ortho-Novum Tablets and Modicon Tablets Prescribing Information, Apr. 2002, 8 pp.
Otake et al. (May 15, 2005) Association of visceral fat accumulation and plasma adiponectin and colorectal ademona: evidence for participation of insulin resistance, Clinical Cancer Research 11:3642-3646.
Ovadia, Oct. 1999, A Novel Twist on Binge Eating Treatment, Psychiatric Dispatches in Primary Psychiatry; 6(10):24-29.
Paar et al., 2002, Bivalent ligands with rigid double-stranded DNA spacers reveal structural constraints on signaling by FcεRI, J. Immunol., 169:856-864.
Padwal, Oct. 6, 2009, Contrave, a bupropion and naltrexone combination therapy for the potential treatment of obesity, Curr. Opin. Investig. Drugs, 10(10):1117-1125 (abstract).
Paile-Hyvarinen et al., Mar. 14, 2003, Quality of life and metabolic status in mildly depressed women with type 2 diabetes treated with paroxetine: a single blind randomised placebo controlled trial, BMC Family Practice, Biomed Central, 4(1), 6 pp.
Pandit 2007, Introduction to the Pharmaceutical Sciences, 1st Ed., Lippincott Williams & Wilkins, Baltimore, MD, p. 154.
Pasternak et al. (1980) Long-acting opiate agonists and antagonists: 14-hydroxydihydromorphinone hydrazones, Med. Chem, 23:674-676.
Pavuluri et al. (2002) Topiramate Plus Risperidone for Controlling Weight Gain and Symptoms in Preschool Mania, Journal of Child and Adolescent Psychopharmacology, 12(3):271-273.
Penn et al., 2003, Pharmacotherapy of obesity in the near term, Current Opinion in Endocrinology and Diabetes, 18(2):311-316.
Portoghese et al., 1982, Opioid agonist and antagonist bivalent ligands as receptor probes, Life Sciences, 31:1283-1286.
Portoghese et al., 1986, Opioid agonist and antagonist bivalent ligands. The relationship between spacer length and selectivity at multiple opioid receptors, J. Med. Chem., 29:1855-1861.
Portoghese et al., 1986, Synthesis and Opioid antagonist potencies of naltrexamine bivalent ligands with conformationally restricted spacers J. Med. Chem., 29:1650-1653.
Portoghese, 1992, The role of concepts in structure-activity relationship studies of opioid ligands, J. Med. Chem., 35:1927-1937.
Potter et al., 1997, Sustained Weight Loss Associated with 12-month topiramate Therapy, Epilepsia, Raven Press Ltd. New York, 38(Suppl 8):97.
Rao et al. (1998) Fixed-dose combination therapy: panacea or poison?, Intensive Care Med, 24:283-285.
Reaven, G. M. 1995. Pathophysiology of insulin resistance in human disease. Physiological Reviews, 75(3):473-486.
Reents et al. (1988) Nalozone and naltrexone, Chest, 93(1):217-219.
Remington's Pharmaceutical Sciences. 18th Edition; Easton, PA: Mack Publishing Co. (1990).
Reneric et al. (Nov. 1998) Opioid Receptor Antagonists in Psychiatry, CNS Drugs, 10(5):365-382.
Rezvani et al. 2000. Combination pharmacotherapy: A mixture of small doses of naltrexone, fluoxetine, and thyrotropin-releasing hormone analogue reduces alcohol intake in three strains of alcohol-preferring rats. Alcohol & Alcoholism, 35(1):76-83.
Romano et al. 2001. Long-term treatment of obsessive-compulsive disorder after an acute response: A comparison of fluoxetine versus placebo. Journal of Clinical Psychopharmacology, 21(1):46-52.
Rotzinger et al. (1999) Metabolism of some 'second' and 'fourth' generation antidepressants: iprindole, viloxazine, bupropion, mianserin, maprotiline, trazadone, nefazodone, and vaniafaxine, Cellular and Molecular Neurobiology, 19:430.
Rowland et al. (2001) Effects of the cannabinoid receptor antagonist SR 141716, alone and in combination with dexfenfluramine or naloxone, on food intake in rats. Psychopharmacology; 159:111-116.
Saba et al. 2002. Lamotrigine-clozapine combination in refractory schizophrenia: Three cases. The Journal of Neuropsychiatry and Clinical Neurosciences, 14(1):86.
Sackellares et al. (1985) Pilot study of zonisamide (1,2-benzisoxazole-3-methanesulfonamide) in patients with refractory partial seizures. Epilepsia, 26(3):206-211.
Saper et al. (2002) The need to feed: Homeostatic and hedonic control of eating, Neuron, 36:199-211.
Sashiwa et al., 2000, Chemical modification of chitosan. 3. Hyperbranched chitosan-sialic acid dendrimer hybrid with tetraethylene glycol spacer, Macromolecules, 33:6913-6915.
Sayre et al., 1984, Design and synthesis of naltrexone-derived affinity labels with nonequilibrium opioid agonist and antagonist

(56) References Cited

OTHER PUBLICATIONS activities. Evidence for the existence of different receptor subtypes in different tissues, J. Med. Chem., 27:1325-1335.
Scheen et al., May 1, 2005, Diabete sucre iatrogene: l'exemple des anti-phsychogiques atypiques, Revue Medicale de Liege, 60(5-6):455-460.
Schimmel et al., 1974, Inhibition by diphenylhydantoin of the diabetogenic action of streptozocin, Horm. Metab. Res. 6:475-477.
Schmidhammer et al. (1994) Mixed Azines of Naloxone with Dihydromorphinone Derivatives. A. Helv. Chim. Acta; 77:999-1002.
Schmidt et al. (1993) Zonisamide for add-on treatment of refractory partial epilepsy: a European double-blind trial. Epilepsy Research; 15:67-73.
Shapira et al. (2000) Treatment of Binge-Eating Disorder with Topiramate: A Clinical Case Series. J. Clin. Psychiatry; 61(5):368-371.
Shapira et al. 2004. A double-blind, placebo-controlled trial of olanzapine addition in fluoxetine-refractory obsessive-compulsive disorder. Biol. Psychiatry, 550:553-555.
Shapiro et al. (2005) Additive Benefits of Combination Therapy with Sibutramine and Rimonabant on Body Weight, Insulin Sensitivity and Lipoproteins in Diet-Induced Obese Mice, 2005 NAASO Annual Meeting, Poster 405-P.
Shelton (2003) Classification of Antidepressants and their Clinical Implications, Primary Care Companion J. Clin. Psychiatry, 5(Supp. 7):27-32.
Shriqui et al. (Jul. 2002) Atypical Antipsychotics, The Canadian Journal of CME, pp. 65-80.
Shuman et al., Jun. 1986, Abnormal body fat distribution detected by computed tomography in diabetic men, Investigative Radiology, 21(6):483-487.
Sitsen et al., 2001, Drug-drug interaction studies with mirtazapine and carbamazepine in healthy male subjects, European Journal of Drug Metabolism and Pharmacokinetics, 26(1-2):109-121.
Sleep Disorders, in Diagnostic and Statistical Manual of Mental Disorders, 4th Edition, American Psychiatric Association, p. 583-595 (2000).
Sneer et al., Protective effect of diphenylhydantoin on the diabetes-inducing effect of alioxan, database accession No. 1980:34024.
Spigset et al. (2001) Therapeutic Approaches to Bulimia Nervosa, Expert Opinion on Therapeutic Patents, 11(3):463-477.
Srivastava et al. 1975. Organic disulfides and related substances. 38. Some disulfide and trisulfide sulfinate salts as antiradiation drugs. Journal of Medicinal Chemistry, 18(8):798-802.
Stansfeld et al., Aug. 1992, Social class and minor psychiatric disorder in British civil servants: a validated screening survey using the General Health Questionnaire, Psychological Medicine, 22:739-749.
Steffen et al. 2006. Emerging drugs for eating disorder treatment. Expert Opin. Emerging Drugs, 11(2):315-336.
Stein (Feb. 15, 2000) Neurobiology of the obsessive-compulsive spectrum disorders, Biological Psychiatry 47(4):296-304.
Stein (Aug. 3, 2002) Obsessive-compulsive disorder, Lancet 360(9330):397-405.
Stepinski et al., 1991, Use of hydrophilic diamines for bridging of two opioid peptide pharmacophores, Internat. J. of Peptide & Protein Res., 38:588-592.
Storch et al. 2006. Clinical predictors of early fluoxetine treatment response in obsessive-compulsive disorder. Depression and Anxiety, 23:429-433.
Stromberg et al. (2002) A comparison of the effects of 6-beta naltrexol and naltrexone on the consumption of ethanol or sucrose using a limited-access procedure in rats. Pharmacology, Biochemistry, and Behavior, 72:483-490.
Swedo et al. 1998. Pediatric autoimmune neuropsychiatric disorders associated with streptococcal infections: Clinical description of the first 50 cases. Am. J. Psychiatry, 155(2):264-271.
Symons et al. 2004. Self-injurious behavior and the efficacy of naltrexone treatment: A quantitative synthesis. Mental Retardation and Developmental Disabilities Research Reviews, 10:193-200.
Tamiz et al., 2000, Application of the bivalent ligand approach to the design of novel dimeric serotonin reuptake inhibitors, J. Am. Chem. Soc., 122:5393-5394.
Tamiz et al., 2001, Pharmacological and behavioral analysis of the effects of some bivalent ligand-based monoamine reuptake inhibitors, J. Med. Chem., 44:1615-1622.
Tavakoli et al., Jul. 2003, Diabetic ketoacidosis in a patient with olanzapine, valproic acid, and venlafaxine, Southern Medical Journal, 96(7):729-730.
Testa, 2004, Prodrug research: futile or fertile?, Biochemical Pharmacology, 68:2097-2106.
Thearle et al. (2003) Obesity and Pharmacology, Endocrinology and Metabolism Clinics of North American, W.B. Suanders Company, Philadelphia US 32(4):1005-1024.
Thombre et al. (2004) Osmotic drug delivery using swellable-core technology, Journal of Controlled Release 94:75-89.
Tollefson et al. (1997) Olanzapine versus haloperidol in the treatment of schizophrenia and schizoaffective and schizophreniform disorders: results of an international collaborative trial, Am J. Psychiatry, 154(5):457-465.
Turnbull et al., Jan. 1985, The effect of valproate on blood metabolite concentrations in spontaneously diabetic, ketoacidotic, bb/e wistar rats, Diabetes Research 2(1):45-48.
Tutka et al., 2004, Convulsant and anticonvulsant effects of bupropion in mice, European Journal of Pharmacology, 499:117-120.
Van Gaal et al., Aug. 1998, Sibutramine and fat distribution: is there a role for pharmacotherapy in abdominal/visceral fat reduction?, Int J Obes Relat Metab Disord, Suppl 1:S38-40; discussion S41-2 (abstract).
Van Schaftingen et al. (1992) The regulatory protein of liver glucokinase. Advan. Enzyme Regul., 32:133-148.
Vieta et al. (2003) 1-year follow-up of patients treated with risperidone and topiramate for a manic episode, J Clin Psychiatry, 64(7):834-829.
Vieta et al. (2004) Effects on weight and outcome of long-term olanzapine-topiramate combination treatment in bipolar disorder. Journal of Clinical Psychopharmacology 24(4):374-378.
Vythilingum et al. 2005. Obsessive-compulsive disorders and dermatologic disease. Dermatologic Clinics, 23:675-680.
Wadden et al. (2000) Effects of Sibutramine Plus Orlistat in Obese Women Following 1 Year of Treatment by Sibutramine Alone: A Placebo-Controlled Trial, Obesity Research; 8(6):431.
Wadden et al., Jan. 2011, Weight loss with naltrexone SR/bupropion SR combination therapy as an adjunct to behavior modification: the COR-BMOD trial, Obesity, 19(1):110-120.
Walker et al. (1988) Chronic Toxicity of the Anticonvulsant Zonisamide in Beagle Dogs, Fundamental and Applied Toxicology 11:333-342.
Wang et al. (2002) Gabapentin augmentation therapy in bipolar depression, Bipolar Disorders 4:296-301.
Weintraub et al. (1992) Long-term Weight Control Study I (weeks 0 to 34) 'The Enhancement of Behavior Modification, Caloric Restriction, and Exercise by Fenfluramine Plus Phentermine versus Placebo', Clinical Pharmacology & Therapeutics, 51(5):586-94.
Welty et al. (Nov. 30-Dec. 5, 2001) Weight Loss Associated With Use of Zonisamide in European and US Clinical Trials, A Compendium of Posters and Platform Sessions for Zonegran®, Presented at the Annual Meeting 2001 of the American Epilepsy Society, Philadelphia, Pennsylvania.
Wermuth, Apr. 2006, Similarity in drugs: reflections on analogue design, Drug Discovery Today, 11(7/8):348-354.
Werneke et al. (2002) Options for Pharmacological Management of Obesity in patients Treated with Atypical Antipsychotics, International Clinical Psychopharmacology, 17(4):145-160.
Wheatley et al., 1998, Mirtazapine: efficacy and tolerability in comparison with fluoxetine in patients with moderate to severe major depressive disorder, J. Clin Psychiatry, 59(6):306-312, Abstract.
White et al. 2002. Development and validation of the food-craving inventory. Obesity Research, 10(2):107-114.
Wieczorek et al., 2001, The effects of the selective serotonin reuptake-inhibitor fluvoxamine on body weight in Zucker rats are

(56) References Cited

OTHER PUBLICATIONS mediated by cortocotrophin-releasing hormone, International Journal of Obesity, 25(10):1566-1569.
Wilcox et al., 2009, An open-label study of naltrexone and bupropion combination therapy for smoking cessation in overweight and obese subjects, Addictive Behaviors, 35(3):229-234.
Wilding (2004) Clinical evaluation of anti-obesity drugs. Current Drug Targets; 5:325-332.
Willmore, L. J. 2004. Commentary on Leppik. Seizure, 13S:S10.
Wilner, 2002, Is Weight Loss With Zonisamide Gender-Specific?, Annual Meeting of the American Epilepsy Society, https://secure.neurohub.net/cgi-perl/get.cgi?pub=52318&ext=htm, 1 pp.
Wolff (1995) Burger's Medicinal Chemistry and Drug Discovery, John Wiley & Sons, 5th Ed. 1:975-977.
Yeomans et al. (2002) Opioid peptides and the control of human ingestive behaviour, Neuroscience and Biobehavioral Reviews, 26:712-728.
Yoshimasu et al. (2003) Psychotropic Drug-Induced Obesity, Nippon Rinsho, 61(Suppl. 6):825-829. (English translation of Japanese Office Action containing Examiner's characterization of reference is appended to reference: Notice of Reasons for Rejection, Application No. 2006-549530).
Yu et al. (2005) Influence of insulin treatment on insulin sensitivity in insulin requiring type 2 diabetes patents, Diabetes Research and Clinical Practice, 68S1:S54-S59.
Zeng et al., 1988, Convenient synthesis of 9-alkyl and 9-arylacridines from [2-(trimethylsilyl)ethoxy]methyl (sem) protected acridone, Tetrahedron Letters, 29(40):5123-5124.
Zhang et al. (1994) Positional Cloning of the Mouse obese gen and its humane homologue, Nature, 372:425-432.
Zhu et al. (Apr. 3, 2002) Pharmacologic Treatment of Eating Disorders, Canadian Journal of Psychiatry, 47(3):227-234.
Zitterl et al. 1999. Efficacy of fluoxetine in Austrian patients with obsessive-compulsive disorder. Wiener Klinische Wochenschrift, 111(11):439-442.
Zohar et al. 1987. Serotonergic responsivity in obsessive-compulsive disorder. Arch. Gen. Psychiatry, 44:946-951.
Zonisamide (Oral Route), MayoClinic.com, 12 pp., 2009.
International Search Report and Written Opinion for PCT/US04/012393, dated Aug. 30, 2004.
International Preliminary Examination Report for PCT/US04/012393, dated Jun. 29, 2005.
A multicenter, randomized, double-blind, placebo-controlled study assessing the occurrence of major adverse cardiovascular events (MACE) in overweight and obese subjects with cardiovascular risk factors receiving naltrexone SR/bupropion SR, Adis Clinical Trials Insight (Nov. 15, 2011), 5 pp.
Aigner et al., 2011, World Federation of Societies of Biological Psychiatry Guideline for the Pharmacological Treatment of Eating Disorders, The world Journal of Biological Psychiatry, 12:400-443.
Altomonte et al., 1988, Effect of fenfluramine on insulin/growth hormone ratio in obese subjects, Pharmacology, 36(2):106-111.
Bakris et al., 2002, Orlistat improves blood pressure and control in obese subjects with treated but inadequately controlled hypertension, Journal of Hypertension, 20(11):2257-2267.
Bengtsson, 1993, The consequences of growth hormone deficiency in adults, Acta Endocrinol. (Copenh.), 128(Suppl 2):2-5.
Brown et al., 2012, Current and emerging directions in the treatment of eating disorders, Substance Abuse: Research and Treatment, 6:33-61.
Brunk, Sep. 1, 2009, Significant weight loss shown with naltrexone/bupropion combo, Thoracic Surgery News, http://www.thoracicsurgerynews.com/?id=95937&tx_ttnews[tt_news]=86987&cHash=a97b7f3c0f6a8c6a3b3ca96df9a6b73f, 1 pp.
Carson et al., May 1996, Pilot study of the use of naltrexone to treat the severe pruritis of cholestatic liver disease, Amer. J. Gastroenterology, 91(5):1022-1023.
Chakraborty et al., 2010, Management of anorexia and bulimia nervosa: an evidence-based review, Indian J Psychiatry, 52:174-186.
Cleveland Clinic Press Release: "Clinical Trial Testing Safety of Obesity Drug Contrave Halted; 50 Percent Interim Data Released by the Study's Executive Committee", May 12, 2015, retrieved from http://my.clevelandclinic.org/about-cleveland-clinic/newsroom/releases-videos-newsletters/2015-5-12-clinical-trial-testing-safety-of-obesity-drug-contrave-halted.
Clinical Trials.gov, A Multicenter, randomized, double-blind, placebo-controlled study assessing the occurrence of major adverse cardiovascular events (MACE) such as cardiovascular death, non-fatal myocardial infarction, and non-fatal stroke in overweight and obese subjects who are at a higher risk of having these events because they ahv diabetes and/or other cardiovascular risk factors, NTC01601704, May 7, 2013, 4 pp.
Clinical Trials.gov, Jul. 13, 2009, An open-label study assessing the safety and efficacy of naltrexone sustained release (SR)/bupropion sustained release (SR) in overweight or obese subjects with major depression, 2 pp.
ClinicalTrials.gov, Apr. 3, 2007, A safety and efficacy study of naltrexone sr/bupropion sr and placebo in overweight and obese subjects participating in an intensive behavior modification program, NCT00456521, 5 pp.
Das et al., 2003, Controlled-release of oral dosage forms, Formulation, Fill & Finish, pp. 10-16.
De Boer et al., 1995, Clinical aspects of growth hormone deficiency in adults, Endocrine Reviews, 16(1):63-86.
Eckel et al., Apr. 16, 2005, The metabolic syndrome, The Lancet 365:1415-1428.
Eid et al., 2005, Effective treatment of polycystic ovarian syndrome with roux-en-y gastric bypass, Surgery for Obesity and Related Diseases, 1:77-80.
Ghisoli et al., 1980, Effects of dopaminergic receptor stimulation and opioid receptor blockade on GH incretion: preliminary findings, Boll. Soc. Ital. Biol. Sper., 56(12):1222-1225.
Ghisoli et al., 1980, Effects of interaction between 2-Br-α-ergocryptine (CB 154) and naloxone on the control of insulin secretion in normal man, Boll. Soc. Ital. Biol. Sper., 56(12):1215-1221.
Glod et al., Jul.-Sep. 2003, Open trial of bupropion sr in adolescent major depression, J Child Adolesc Psychiatr Nurs, 16(3):123-130.
Goodman & Gillman's, The Pharmacological Basis of Therapeutics, 10th Ed., Edited by J. Hardman and L. Limbird, 2001, p. 6.
Guidance for Industry Estimating the Maximum Safe Starting Dose in Initial Clinical Trials for Therapeutics in Adult Healthy Volunteers, U.S. Department of Health and Human Services, U.S. Food and Drug Administration Center for Drug Evaluation and Research (CDER), Pharmacology and Toxicology, Jul. 2005.
Halford et al., May 2010, Pharmacological mangement of appetite expression in obesity, Nature Reviews Endocrinology, 6(5):255-269.
Herper, "A Top Cardiologist Says a Diet Drug Maker Misled Patients and Investors", Forbes, May 12, 2015, retrieved from http://www.forbes.com/sites/matthewherper/2015/05/12/a-top-cardiologist-says-a-diet-drug-maker-misled-patients-and-investors/#.
Herper, "Heart Benefit for Orexigen Drug Nearly Vanishes with New Data", Forbes, May 12, 2015, retrived from http://www.forbes.com/sites/matthewherper/2015/05/12/heart-benefit-for-orexigen-drug-nearly-vanishes-with-new-data/.
Herper, Mar. 5, 2015, Top FDA Official Says Orexigen Study Result 'Unreliable,' Misleading, http://www.forbes.com/sites/matthewherper/, 4 pp.
Hollander et al., Oct. 21, 2013, Effects of naltrexone sustained-release/bupropion sustained release combination therapy on body weight and glycemic parameters in overweight and obese patents with type 2 diabetes, Diabetes Care, 36(12):4022-4029.
Husten, Mar. 3, 2015, Orexigen Released Interim Data Without Approval of Trial Leaders, http://ww/forbes.com/sites/harryhusten, 6 pp.
Ioannides-Demos et al., 2005, Pharmacotherapy for obesity, Drugs, 65(10):1391-1418.
Johannsson et al., 1997, Growth hormone treatment of abdominally obese men reduces abdominal fat mass, improves glucose and

(56) References Cited

OTHER PUBLICATIONS lipoprotein metabolism, and reduces diastolic blood pressure, J. Clin. Endocrin. and Metab., 82(3):727-734.
Johnston et al., 2002, Pharmacokinetic optimization of sustained-release bupropion for smoking cessation, Drugs, 62(Suppl. 2):11-24.
Katsiki et al., Jun. 1, 2011, Naltrexone sustained-release (SR) + bupropion SR combination therapy for the treatment of obesity: 'a new kid on the block'?, Annals of Medicine, 43(4):249-258.
Kelley et al., 2000, A pharmacological analysis of the substrates underlying conditioned feeding induced by repeated opioid stimulation of the nucleus accumbens, Neuropsychopharmacology, 23(4):455-467.
Klein et al., Jun. 1, 2009, Naltrexone plus bupropion combination causes significant weight loss without worsening psychiatric symptoms, Diabetes, 58(Suppl. 1):A444, Abstract 1739-P.
Kruger, 2000, Psychotherapy of anorexia nervosa, bulimia nervosa and binge-eating disorder, J. Psychiatry Neurosci, 25(5):497-508.
Laessle et al., May 1997, A comparison of resting metabolic rate, self-rated food intake, growth hormone, and insulin levels in obese and nonobese preadolescents, Physiol. Behav., 61(5):725-729.
Ludman et al., "Does depression reduce the effectiveness of behavioral weight loss treatment?" Behav Med. 2010; 35(4):126-134 (abstract).
McElroy et al., Jun. 1, 2010, An open-label study evaluating the naltrexone SR/bupropion SR combination therapy in overweight or obese subjects with major depression, Diabetes, 59(Suppl. 1):A483.
McElroy et al., Jun. 2013, Naltrexone/bupropion combination therapy in overweight or obese patients with major depressive disorder: results of a pilot study, Prim Care Companion CNS Disord, 15(3), 17 pp.
McElroy et al., May 7, 2012, Pharmacological management of binge-eating disorder: current and emerging treatment options, Therapeutics and Clinical Risk Management, 8:219-241.
Melander, Oct. 1978, Influence of food on the bioavailability of drugs, Clinical Pharmacokinetics, 3(5):337-351.
Meyer et al., Sep. 1984, Bioequivalence, dose-proportionality, and pharmacokinetics of naltrexone after oral administration, J. Clin. Psychiatry, 45(9)(Sec. 2):15-19.
Milano et al., May-Jun. 2005, Treatment of bulimia nervosa with fluvoxamine: a randomized controlled trial, Advances in Therapy, 22(3):278-283.
Miyazaki, 2005, Adiposity and Drug Treatment, Resident Notes, 7(4):499-502.
Mukherjee, "Update: Takeda threatens to break off Orexigen collab after Contrave data drama", BioPharmaDive, May 13, 2015, retrieved from http://www.biopharmadive.com/news/update-takeda-threatens-to-break-off-orexigen-collab-after-contrave-data-d/396940/.
Oncken et al., 2001, Adverse effects of Oral naltrexone: an analysis of data from two clinical trials, Psychopharmacology, 154:397-402.
Orexigen Therapeutics Press Release: "Orexigen Therapeutics Provides Statement on Termination of the Light Study and Updates on Contrave Collaboration with Takeda Pharmaceuticals", May 12, 2015, retrieved from http://ir.orexigen.com/phoenix.zhtml?c=207034&p=irol-newsArticle_Print&ID=2047312.
Orexigen Therapeutics Press Release: "Takeda Pharmaceuticals and Orexigen Therapeutics Announce Termination of the Cardiovascular Outcomes Study (Light Study) of the Obesity Drug Contrave® (naltrexone HCI and bupropion HCI)", May 12, 2015, retrieved from http://ir.orexigen.com/phoenix.zhtml?c=207034&p=irol-newsArticle_Print&ID=2046959.
Orexigen Therapeutics, Inc., 2008, A safety and efficacy study comparing naltrexone SR/bupropion SR and placebo in obese type 2 diabetics, http://clinicaltrials.gov/ct2/show/NCT00474630, 3 pp.
Orexigen Therapeutics, Inc., Method-of-use study assessing the effect of naltrexone sustained release (SR)/bupropion SR on body weight and cardiovascular risk factors in overweight and obese subjects, http://clinicaltrials.gov/ct2/show/NCT01764386, 5 pp. Feb. 9, 2013.

Pagoto et al., Association of Major Depression and Binge Eating Disorder with Weight Loss in a Clinical Setting, Obesity, Nov. 2007; 15(11):2557-2559.
Patel et al., Jun. 2011, A hospital-based observational study of type 2 diabetic subjects from Gujarat, India, Journal of Health, Population and Nutrition, 29(3):265-272.
Pearlstein et al., 2003, A double-blind, placebo-controlled trial of fluvoxamine in binge eating disorder; a high placebo response, Arch Womens Ment Health, 6:147-151.
Plodkowski et al., 2009, Bupropion and naltrexone: a review of their use individually and in combination for the treatment of obesity, Expert Opin. Pharmacother. 10(6):1069-1081.
Ramlo-Halsted et al., 2000, The natural history of type 2 diabetes: practical points to consider in developing prevention and treatment strategies, Clin. Diabetes, 18(2).
Rao, Mar. 2001, Insulin resistance syndrome, American Family Physician, 63(6):1159-1163.
Remington's Pharmaceutical Sciences, 1980, 16th ed., Mack Publishing Company, Arthur Osol. Editor, pp. 1553-1584.
Remington's Pharmaceutical Sciences, 1980, 16th ed., Mack Publishing Company, Arthur Osol. Editor, pp. 1594-1613.
Ricca et al., 2001, Fluoxetine and fluvoxamine combined with individaul congitive-behavior therapy in binge-eating disorder: a one-year follow-up study, Psychotherapy and Psychosomatics, 70:298-306.
Richelsen et al., Feb. 1994, Growth hormone treatment of obese women for 5 wk: effect on body composition and adipose tissue LPL activity, Am J. Physiol., 266(2 Pt 1):11-16.
Schneider et al., Sep. 15, 2009, Design and methods for a randomized clinical trial treating comorbid obesity and major depressive disorder, BMC Psychiatry, 8:77.
Stedman's Medical Dictionary, 28th ed., Lippincott Williams & Wilkins, Philadelphia, 1999, pp. 490-491 and 1552.
Tallarida et al., 1996, Testing for synergism over a range of fixed ratio drug combinations: replacing the isobologram, Life Sciences, 58(2):PL23-PL28.
Tallarida, 2001, Drug synergism: its detection and applications, J. Pharmacol. and Expt. Therap., 298(3):865-872.
Wellbutrin® (bupropion hydrochloride) tablets, in Physicians' Desk Reference, 49th edition, 1995, pp. 824-827, 150.
White et al., 2003, Clarifying the role of insulin in type 2 diabetes management, Clinical Diabetes, 21(1):14-21.
Winstanley et al., 1989, The effects of food on drug bioavailability, Br. J. clin. Pharmac. 28:621-628.
Wong et al., Aug. 2004, Starting insulin treatment in type 2 diabetes, Australian Prescriber, 27(4):93-96.
Trexan® (naltrexone hydrochloride), in Physicians' Desk Reference, 49th edition, 1995, pp. 965-967.
Verebey, Quantitative determination of naltrexone, 6 β-naltrexol and 2-hydroxy-3-methoxy-6 β-naltrexol (HMN) in human plasma, red blood cells, saliva and urine by gas liquid chromatography, National Institute on Drug Abuse Research Monograph Series, 1981; 28:36-51.
Verebey, The clinical pharmacology of naltrexone: pharmacology and pharmacodynamics, National Institute on Drug Abuse Research Monograph Series, 1981; 28:147-158.
Wall et al., Metabolism and disposition of naltrexone in man after oral and intravenous administration, Drug Metabolism and Disposition, Jul./Aug. 1981, 9(4):369-375.
Bradley et al., Aug. 2002, Bupropion SR versus placebo: comparison of depressive symptoms and weight loss in obese patients with a history of major depression, International Journal of Obesity, 26(Suppl. 1):S156.
ClinicalTrials.gov archive, Feb. 5, 2010, A phase 3 study comparing the safety and efficacy of two doses of naltrexone sustained release (SR)/bupropion sustained release (SR) and placebo in obese subjects, NCT00532779, 3 pp.
Defendant Actavis Laboratories FL, Inc.'s Initial Invalidity Contentions for U.S. Pat. No. 9,125,868, in *Takeda Pharmaceutical Company Limited et al.*, Plaintiffs, v. *Actavis Laboratories FL, Inc.*, Defendant, C.A. No. 15-451-RGA, US District Court for the District of Delaware, dated Jul. 25, 2016, 48 pp.

(56) References Cited

OTHER PUBLICATIONS

Defendant Actavis Laboratories FL, Inc.'s Initial Invalidity Contentions for U.S. Pat. Nos. 7,375,111, 7.462,626, and 8,916,195, in *Takeda Pharmaceutical Company Limited et al.*, Plaintiffs, v. *Actavis Laboratories FL, Inc.*, Defendant, C.A. No. 15-451-RGA, US District Court for the District of Delaware, dated Dec. 23, 2015, 147 pp.
Dramatic alcohol treatment results seen with naltrexone, Psychiatric Times, Sep. 1, 1998, 4 pp.
Drugs.com, Sep. 20, 2011, Orexigen and FDA identify a clear and feasible path to approval for contrave, http://www.drugs.com/nda/contrave_110920.html, 4 pp.
GlaxoSmithKline, Jun. 2009, Prescribing Information: Wellbutrin® (bupropion hydrochloride) Tablets, pp. 4-32.
Goodpaster et al., Feb. 2003, Association between regional adipose tissue distribution and both type 2 diabetes and impaired glucose tolerance in elderly men and women, Diabetes Care, 26(2):372-379.
Greenway et al., Jun. 10, 2008, Naltrexone and bupropion reduce the prevalence of the metabolic syndrom, Diabetes, 57(Suppl. 1), Abstract No. 2735-PO.
Grundy et al., 2005, Diagnosis and management of the metabolic syndrome, Circulation, 112:2735-2752.
McElroy et al., Nov. 2010, Reduced depressive symptoms and weight loss in depressed overweight/obese subjects completing 24 weeks of open label therapy with naltrexone sr/bupropion sr, 18(Supp 2):S152.
Miller et al., May 2006, Metabolic syndrome: screening, diagnosis, and management, Journal of Midwifery & Women's Health, 51(3):141-151.
NIH News Release, First federal obesity clinical guidelines released, Jun. 17, 1998.
Orexigen Therapeutics Press Release, Feb. 1, 2011, FDA issues complete response to new drug application for Contrave® for the management of obesity, 3 pp.
Pfizer Inc., Apr. 2014, Embeda Prescription Information, 34 pp.
Remington's Pharmaceutical Sciences, 1980, 16th ed., Mack Publishing Company, Arthur Osol. Editor, pp. 1592-1597, 1676-1678.
Spiegel et al., 1987, Effect of naltrexone on food intake, hunger, and satiety in obese men, Physiology & Behavior, 40(2):135-141.
White et al., 2013, Buproprion for overweight women with binge-eating disorder: a randomized, double-blind, placebo-controlled trial, J. Clin. Psychiatry, 74(4):400-406.

\* cited by examiner

COMPOSITIONS FOR AFFECTING WEIGHT LOSS

RELATED APPLICATIONS

The present application is a continuation of U.S. application Ser. No. 14/602,154, filed Jan. 21, 2015, which is a continuation of U.S. application Ser. No. 13/241,023, filed Sep. 22, 2011, which is a continuation of U.S. application Ser. No. 12/751,970, filed Mar. 31, 2010, now abandoned, which is a continuation of U.S. application Ser. No. 11/779,008, filed Jul. 17, 2007, now abandoned, which is a continuation of U.S. application Ser. No. 10/828,795, filed Apr. 21, 2004, now U.S. Pat. No. 7,375,111, which claims the benefit of priority to U.S. Provisional Application No. 60/466,838, filed on Apr. 29, 2003, all of which are hereby incorporated by reference in their entireties.

BACKGROUND OF THE INVENTION

Field of the Invention

The present invention is in the field of pharmaceutical compositions and methods for the treatment of obesity and for affecting weight loss in individuals.

Description of the Related Art

Obesity is a disorder characterized by the accumulation of excess fat in the body. Obesity has been recognized as one of the leading causes of disease and is emerging as a global problem. Increased instances of complications such as hypertension, non-insulin dependent diabetes mellitus, arteriosclerosis, dyslipidemia, certain forms of cancer, sleep apnea, and osteoarthritis have been related to increased instances of obesity in the general population.

Obesity has been defined in terms of body mass index (BMI). BMI is calculated as weight $(kg)/[height\ (m)]^2$. According to the guidelines of the U.S. Centers for Disease Control and Prevention (CDC), and the World Health Organization (WHO) (World Health Organization. Physical status: The use and interpretation of anthropometry. Geneva, Switzerland: World Health Organization 1995. *WHO Technical Report Series*), for adults over 20 years old, BMI falls into one of these categories: below 18.5 is considered underweight, 18.5-24.9 is considered normal, 25.0-29.9 is considered overweight, and 30.0 and above is considered obese.

Prior to 1994, obesity was generally considered a psychological problem. The discovery of the adipostatic hormone leptin in 1994 (Zhang et al., "Positional cloning of the mouse obese gene and its human homologue," Nature 1994; 372:425-432) brought forth the realization that, in certain cases, obesity may have a biochemical basis. A corollary to this realization was the idea that the treatment of obesity may be achieved by chemical approaches. Since then, a number of such chemical treatments have entered the market. The most famous of these attempts was the introduction of Fen-Phen, a combination of fenfluramine and phentermine. Unfortunately, it was discovered that fenfluramine caused heart-valve complications, which in some cases resulted in the death of the user. Fenfluramine has since been withdrawn from the market. There has been some limited success with other combination therapy approaches, particularly in the field of psychological eating disorders. One such example is Devlin, et al., Int. J. Eating Disord. 28:325-332, 2000, in which a combination of phentermine and fluoxetine showed some efficacy in the treatment of binge eating disorders. Of course, this disorder is an issue for only a small portion of the population.

In addition to those individuals who satisfy a strict definition of medical obesity, a significant portion of the adult population is overweight. These overweight individuals would also benefit from the availability of an effective weight-loss composition. Therefore, there is an unmet need in the art to provide pharmaceutical compositions that can affect weight loss without having other adverse side effects.

SUMMARY OF THE INVENTION

Disclosed are compositions for affecting weight loss comprising a first compound and a second compound, where the first compound is an opioid antagonist and the second compound causes increased agonism of a melanocortin 3 receptor (MC3-R) or a melanocortin 4 receptor (MC4-R) compared to normal physiological conditions.

Also disclosed are methods of affecting weight loss, increasing energy expenditure, increasing satiety in an individual, or suppressing the appetite of an individual, comprising identifying an individual in need thereof and treating that individual to antagonize opioid receptor activity and to enhance α-MSH activity.

DETAILED DESCRIPTION OF THE PREFERRED EMBODIMENTS

Arcuate nucleus neurons are known to be responsive to a wide array of hormones and nutrients, including leptin, insulin, gonadal steroids, and glucose. In addition to potential transport mechanisms, peripheral substances may access these neurons via arcuate cell bodies in and projections to the median eminence, a region considered to be a circumventricular organ, which lacks a blood-brain barrier. Cone et al., "The arcuate nucleus as a conduit for diverse signals relevant to energy homeostasis," Int'l Journal of Obesity (2001) 25, Suppl 5, S63-S67.

Administration of exogenous leptin activates a number of different neurons in hypothalamic and brainstem cell groups that bear leptin receptor. Leptin-responsive neurons in the arcuate nucleus include both those containing neuropeptide Y (NPY) and agouti-related peptide (AgRP) in the medial part of the nucleus and those containing both pro-opiomelanocortin (POMC) and its derivatives, including α-melanocyte stimulating hormone (α-MSH), as well as cocaine and amphetamine-related transcript (CART). Saper et al., "The need to feed: Homeostatic and hedonic control of eating," Neuron, 36:199-211 (2002).

The leptin-responsive POMC neurons in the arcuate nucleus are thought to cause anorexia and weigh reduction by means of the action of α-MSH on melanocortin 3 and/or 4 receptors (MC3-R, MC4-R). The highest MC3-R expression level is in the hypothalamus and limbic system, whereas MC4-R mRNA is expressed in virtually all major brain regions. Some of the metabolic effects resulting from stimulation of MC4-R are decreased food intake and an increase in energy expenditure through stimulation of thyrotropin-releasing hormone and activation of the sympathetic nervous system. Targeted deletion of the MC4-R gene produces obesity, hyperphagia, hyperinsulinemia, and reduced energy expenditure. Targeted deletion of MC3-R results in increased adiposity due to decreased energy expenditure. Korner et al., "The emerging science of body weight regulation and its impact on obesity treatment," J. Clin. Invest. 111(5):565-570 (2003). Thus, increased concentrations of α-MSH in the central nervous system (CNS) increase its action on MC3-R and/or MC4-R and result in a suppressed appetite.

POMC neurons also release β-endorphin when they release α-MSH. β-endorphin is an endogenous agonist of the μ-opioid receptors (MOP-R), found on the POMC neurons. Stimulation of MOP-R decreases the release of α-MSH. This is a biofeedback mechanism that under normal physiological conditions controls the concentration of α-MSH in the CNS. Thus, blocking MOP-R by opioid antagonists will break the feedback mechanism, which results in continued secretion of α-MSH and an increase in its concentration in the CNS.

A second population of neurons in the arcuate nucleus tonically inhibits the POMC neurons. These POMC-inhibiting neurons secrete NPY, the neurotransmitter γ-aminobutyric acid (GABA), and AgRP. NPY and GABA inhibit POMC neurons, via NPY Y1 receptors and GABA receptors, respectivley. Thus, within the arcuate nucleus NPY and GABA inhibit the release of α-MSH, and therefore are stimulators of feeding. It is known that leptin inhibits the release of GABA from NPY terminals synapsing onto POMC neurons, whereas ghrelin, an orexigenic peptide, stimulates the ghrelin receptors on NPY neurons and increase the secretion of NPY and GABA onto the POMC cells, which in turn inhibits the release of α-MSH.

AgRP stimulates food intake in the rat through antagonism of the interaction of α-MSH at MC4-R. Expression of the AgRP gene is suppressed by leptin.

Serotonin, also known as 5-hydroxytryptamine or 5-HT, activates the POMC neurons to secrete α-MSH. However, serotonin is taken up and removed from action by specific transporters so that a single serotonin molecule has short term effects. It is known that selective serotonin re-uptake inhibitors (SSRIs) prevent the uptake of serotonin and increase its concentrations in the CNS. Thus, SSRIs also increase the secretion of α-MSH and its concentrations in the CNS.

Dopamine also increases the activity of POMC neurons to secrete α-MSH. Like serotonin, dopamine is also taken up and removed from action so that a single dopamine molecule has short term effect. Dopamine re-uptake inhibitors, which prevent or reduce the uptake of dopamine, can also increase the secretion of α-MSH and its concentrations in the CNS.

Therefore, increased secretion of α-MSH through various mechanisms, such as serotonin re-uptake inhibition, are among the strategies that the methods and pharmaceutical compositions of the present invention pursue in order to produce a biochemical anorexigenic effect.

The present invention provides a multi-faceted combination therapy approach to the problem of weight loss. It addresses not just single molecules, messengers, or receptors, but instead acts on multiple points in the feeding and satiety pathway. Aspects of the present invention are directed to increasing the concentrations of α-MSH in the CNS by stimulating the release of α-MSH, suppressing its metabolism, reducing the antagonism of its interaction at MC3/4-R, and suppressing any feedback mechanisms that slow or stop its release. Aspects of the present invention include pharmaceutical compositions whose components achieve one or more of these functions. The present inventors have discovered that a combination of two or more of the compounds disclosed herein results in a synergistic effect that affects weight loss more quickly and on a more permanent basis.

Thus, in a first aspect, the present invention is directed to a composition for the treatment of obesity or for affecting weight loss comprising a first compound and a second compound, where the first compound is an opioid antagonist and the second compound causes increased agonism of a melanocortin 3 receptor (MC3-R) or a melanocortin 4 receptor (MC4-R) compared to normal physiological conditions.

In certain embodiments, the second compound causes increased activity of the POMC neurons, leading to greater agonism at MC3-R and/or MC4-R.

In certain embodiments the opioid antagonist antagonizes a μ-opioid receptor (MOP-R) in a mammal. The mammal may be selected from the group consisting of mice, rats, rabbits, guinea pigs, dogs, cats, sheep, goats, cows, primates, such as monkeys, chimpanzees, and apes, and humans.

In some embodiments the opioid antagonist is selected from the group consisting of alvimopan, norbinaltorphimine, nalmefene, naloxone, naltrexone, methylnaltrexone, and nalorphine, and pharmaceutically acceptable salts or prodrugs thereof.

In other embodiments, the opioid antagonist is a partial opioid agonist. Compounds of this class have some agonist activity at opioid receptors. However, because they are weak agonists, they function as de-facto antagonists. Examples of partial opioid agonists include pentacozine, buprenorphine, nalorphine, propiram, and lofexidine.

The term "pharmaceutically acceptable salt" refers to a formulation of a compound that does not cause significant irritation to an organism to which it is administered and does not abrogate the biological activity and properties of the compound. Pharmaceutical salts can be obtained by reacting a compound of the invention with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical salts can also be obtained by reacting a compound of the invention with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl) methylamine, and salts thereof with amino acids such as arginine, lysine, and the like.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate palatability or be easier to formulate. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to provide the active moiety.

In certain embodiments, the second compound in the pharmaceutical compositions of the present invention triggers the release of α-melanocyte stimulating hormone (α-MSH). The second compound may increase the extracellular serotonin concentrations in the hypothalamus. In some embodiments, the second compound is selected from the group consisting of a selective serotonin reuptake inhibitor (SSRI), a serotonin 2C agonist, and a serotonin 1B agonist. In further embodiments, the second compound is selected, e.g., from the group consisting of fluoxetine, fluvoxamine, sertraline, paroxetine, citalopram, escitalopram, sibutramine, duloxetine, and venlafaxine, and pharmaceutically acceptable salts or prodrugs thereof.

The terms "serotonin 1B receptor," "serotonin 2C receptor," "5-HT1b receptor," and "5-HT2c receptor" refer to receptors found more commonly in rodents. It is understood by those of skill in the art that other mammals have serotonin receptors on various neurons that are analogous in function and form to these receptors. Agonists or antagonists at these non-rodent, preferably human, serotonin receptors are within the scope of the present invention.

In certain embodiments, the second compound suppresses the expression of the AgRP gene or the production or release of agouti-related protein (AgRP). In some of these embodiments, the second compound suppresses the activity of neurons that express AgRP.

In other embodiments, the second compound suppresses the expression of the NPY gene or the production or release of neuropeptide Y (NPY). In some of these embodiments, the second compound suppresses the activity of neurons that express NPY. In further embodiments, the second compound is selected from the group consisting of NPY antagonists, ghrelin antagonists, and leptin. In certain other embodiments, the second compound agonizes NPY Y2 receptor.

Other embodiments of the present invention include those in which the second compound is selected from the group consisting of a γ-amino butyric acid (GABA) inhibitor, a GABA receptor antagonist, and a GABA channel antagonist. By "GABA inhibitor" it is meant a compound that reduces the production of GABA in the cells, reduces the release of GABA from the cells, or reduces the activity of GABA on its receptors, either by preventing the binding of GABA to GABA receptors or by minimizing the effect of such binding. The GABA inhibitor may be a 5-HT1b agonist or another agent that inhibits the activity of NPY/AgRP/GABA neurons. In addition, the GABA inhibitor may suppress the expression of the AgRP gene, or the GABA inhibitor may suppress the production or release of AgRP. It is, however, understood that a 5-HT1b agonist may inhibit the NPY/AgRP/GABA neuron (and therefore activate POMC neurons) without acting as an inhibitor of the GABA pathway.

In certain other embodiments the GABA inhibitor increases the expression of the POMC gene. In some of these embodiments, the GABA inhibitor increases the production or release of pro-opiomelanocortin (POMC) protein. In certain other of these embodiments, the GABA inhibitor increases the activity on POMC expressing neurons. In some embodiments, the GABA inhibitor is topiramate.

In other embodiments the second compound is a dopamine reuptake inhibitor. Phentermine is an example of a dopamine reuptake inhibitor. In certain other embodiments, the second compound is a norepinephrine reuptake inhibitor. Examples of norepinephrine reuptake inhibitors include bupropion, thionisoxetine, and reboxetine. Other embodiments include those in which the second compound is a dopamine agonist. Some dopamine agonists that are available on the market include cabergoline, amantadine, lisuride, pergolide, ropinirole, pramipexole, and bromocriptine. In further embodiments, the second compound is a norepinephrine releaser, for example diethylpropion, or a mixed dopamine/norepinephrine reuptake inhibitor, for example, atomoxatine.

In certain other embodiments, the second compound is a 5-HT1b agonist, such as sumatriptan, almotriptan, naratriptan, frovatriptan, rizatriptan, zomitriptan, and elitriptan.

In further embodiments, the second compound is an anticonvulsant. The anticonvulsant may be selected from the group consisting of zonisamide, topiramate, nembutal, lorazepam, clonazepam, clorazepate, tiagabine, gabapentin, fosphenytoin, phenytoin, carbamazepine, valproate, felbamate, levetiracetam, oxcarbazepine, lamotrigine, methsuximide, and ethosuximide.

In certain embodiments, the second compound itself may be a combination of two or more compounds. For example, the second compound may be a combination of a dopamine reuptake inhibitor and a norepinephrine reuptake inhibitor, e.g. bupropion and mazindol. Alternatively, the second compound may be a combination of a SSRI and a norepinephrine reuptake inhibitor, such as sibutramine, venlafaxine, and duloxetine.

In certain embodiments, the second compound is an activator of the POMC neurons. Examples of POMC activators include Ptx1 and interleukin 1 beta, (IL-1β).

In another aspect, the present invention relates to a method of affecting weight loss, comprising identifying an individual in need thereof and treating that individual to antagonize opioid receptor activity and to enhance α-MSH activity.

In certain embodiments, the individual has a body mass index (BMI) greater than 25. In other embodiments, the individual has a BMI greater than 30. In still other embodiments, the individual has a BMI greater than 40. However, in some embodiments, the individual may have a BMI less than 25. In these embodiments, it may be beneficial for health or cosmetic purposes to affect weight loss, thereby reducing the BMI even further.

In some embodiments, opioid receptor activity is antagonized by administering an opioid receptor antagonist. The opioid receptor antagonist may be a MOP receptor antagonist. In some embodiments, the opioid receptor antagonist is selected from alvimopan, norbinaltorphimine, nalmefene, naloxone, naltrexone, methylnaltrexone, and nalorphine, and pharmaceutically acceptable salts or prodrugs thereof.

In some of the embodiments set forth above, α-MSH activity is enhanced by administering a compound, where the compound triggers release of α-MSH or increases the activity of neurons that express α-MSH. In some embodiments, the compound is a selective serotonin reuptake inhibitor (SSRI) or a specific 5-HT receptor agonist. Examples of SSRIs that can be used in the present invention include fluoxetine, fluvoxamine, sertraline, paroxetine, citalopram, escitalopram, sibutramine, duloxetine, and venlafaxine, and pharmaceutically acceptable salts or prodrugs thereof.

In other embodiments, the compound is a γ-amino butyric acid (GABA) inhibitor. The GABA inhibitor may be a 5-HT1b receptor agonist. The GABA inhibitor may suppress the expression of the AgRP gene, or it may suppresses the production or release of AgRP. The GABA inhibitor may suppress the expression or release of NPY. In certain embodiments, the GABA inhibitor suppresses the activity of neurons that express AgRP. For example, the GABA inhibitor may be topiramate, 1-(2-(((diphenylmethylene)amino)oxy)ethyl)-1,2,5,6-tetrahydro-3-pyridinecarboxylic acid hydrochloride (NNC-711), or vigabatrin.

In certain embodiments, the method of invention set forth above is practiced with the proviso that the individual is not suffering from Prader-Willi syndrome or binge eating disorder. Thus, some embodiments of the invention are to be distinguished from combination therapy involving SSRI anti-depressants (e.g., fluoxetine) used to treat physiological eating disorders such as binge eating disorder or Prader-Willi syndrome. In these embodiments, the target population is the population of individuals needing or desiring weight loss, apart from needing treatment for Prader-Willi syndrome or binge eating disorder.

Individuals suffering from depression may gain weight as a result of their depression. In addition, certain depressed individuals gain weight as a side effect of the depression therapy. In certain embodiments, the method of invention set forth above is practiced with the proviso that the individual is not suffering from depression. In some embodiments, the individual's overweight state was not caused by treatment for depression.

In other embodiments, the method of the invention set forth above is practiced with the proviso that if the opioid receptor is antagonized using naltrexone, then release of α-MSH is not stimulated with fluoxetine. However, the combination of naltrexone with fluoxetine may be used to affect weight loss in individuals who wish to lose weight, whether or not they are clinically categorized as obese. These individuals may include those with BMI of greater than 25, or those individuals with BMI of less than 25 who still wish to lose additional weight. This particular combination may also be used for the treatment of general obesity. In certain embodiments, the individual who wishes to lose additional weight does not suffer from binge eating disorder.

In some embodiments, the treating step of the above method comprises administering to the individual a first compound and a second compound, where the first compound is an opioid antagonist and the second compound enhances α-MSH activity.

In some embodiments the first compound and the second compound are administered more or less simultaneously. In other embodiments the first compound is administered prior to the second compound. In yet other embodiments, the first compound is administered subsequent to the second compound.

In certain embodiments, the first compound and the second compound are administered individually. In other embodiments, the first compound and the second compound are covalently linked to each other such that they form a single chemical entity. The single chemical entity is then digested and is metabolized into two separate physiologically active chemical entities, one of which is the first compound and the other one is the second compound.

In some embodiments, the compositions of the present invention are a combination of the following compounds:

a SSRI in combination with a dopamine reuptake inhibitor, a dopamine/norepinephrine reuptake inhibitor, a norepinephrine reuptake inhibitor, an opioid antagonist, a partial opioid agonist, GABA inhibitor, a peripherally acting weight loss agent such as metformin, or a peptide, such as PYY, $PYY_{3-36}$, or leptin;

Serotonin in combination with a dopamine reuptake inhibitor, a dopamine/norepinephrine reuptake inhibitor, an opioid antagonist, a partial opioid agonist, or a GABA inhibitor;

a dopamine reuptake inhibitor in combination with a norepinephrine reuptake inhibitor, a norepinephrine releaser, a norepinephrine agonist, an opioid antagonist, a partial opioid agonist, a GABA inhibitor, an adenosine compound, a cholinergic receptor antagonist, or a peptide, such as PYY, $PYY_{3-36}$, or leptin;

a dopamine/norepinephrine reuptake inhibitor in combination with an opioid antagonist, a partial opioid agonist, a GABA inhibitor, or a peripherally acting weight loss agent such as metformin;

a dopamine agonist in combination with an opioid antagonist, a partial opioid agonist, a GABA inhibitor, or a peptide, such as PYY, $PYY_{3-36}$, or leptin.

Examples of norepinephrine agonists include phendimetrazine and benzphetamine. Examples of adenosine compounds include all xanthine derivatives, such as adenosine, caffeine, theophylline, theobromine, and aminophylline. An example of a cholinergic receptor antagonist is nicotine.

In another aspect, the present invention relates to a method of increasing satiety in an individual comprising identifying an individual in need thereof and treating that individual to antagonize opioid receptor activity and to enhance α-MSH activity.

In some embodiments, the treating step of the above method comprises administering to the individual a first compound and a second compound, where the first compound is an opioid antagonist and the second compound enhances α-MSH activity.

In some embodiments the first compound and the second compound are administered nearly simultaneously. In other embodiments the first compound is administered prior to the second compound. In yet other embodiments, the first compound is administered subsequent to the second compound.

In yet another aspect, the present invention relates to a method of suppressing the appetite of an individual comprising identifying an individual in need thereof and treating that individual to antagonize opioid receptor activity and to enhance α-MSH activity.

In some embodiments, the treating step of the above method comprises administering to the individual a first compound and a second compound, where the first compound is an opioid antagonist and the second compound enhances α-MSH activity.

In some embodiments the first compound and the second compound are administered nearly simultaneously. In other embodiments the first compound is administered prior to the second compound. In yet other embodiments, the first compound is administered subsequent to the second compound.

In another aspect, the present invention relates to a method of increasing energy expenditure in an individual comprising identifying an individual in need thereof and treating that individual to antagonize opioid receptor activity and to enhance α-MSH activity.

In some embodiments, the treating step of the above method comprises administering to the individual a first compound and a second compound, where the first compound is an opioid antagonist and the second compound enhances α-MSH activity.

In some embodiments the first compound and the second compound are administered nearly simultaneously. In other embodiments the first compound is administered prior to the second compound. In yet other embodiments, the first compound is administered subsequent to the second compound.

In certain embodiments disclosed herein, an individual is given a pharmaceutical composition comprising a combination of two or more compounds to affect weight loss. In some of these embodiments, each compound is a separate chemical entity. However, in other embodiments, the two compounds are joined together by a chemical linkage, such as a covalent bond, so that the two different compounds form separate parts of the same molecule. The chemical linkage is selected such that after entry into the body, the linkage is broken, such as by enzymatic action, acid hydrolysis, base hydrolysis, or the like, and the two separate compounds are then formed.

Thus, in another aspect, the present invention relates to synthetic routes to novel molecules in which an opioid antagonist is linked by a flexible linker to a selective serotonin reuptake inhibitor (SSRI).

Data from previous structure-activity relationship (SAR) studies within the family of μ opioid antagonists may be used as a guide to determine which antagonists to use and the optimal position or positions on the antagonist molecules to attach the tether such that potency and selectivity of the antagonist will remain high. Similarly, SAR data within the family of SSRIs may be used as a guide to determine which inhibitors to use and the optimal position or positions on the inhibitors to attach the tether such that potency and selectivity remain high. The tether or linker moiety is chosen from among those of demonstrated utility for linking bioactive molecules together. Disclosed herein are representative opioid antagonists, linkers and SSRI molecules that can be attached together in different combinations to form heterobivalent therapeutic molecules.

Structure-activity relationships of the opioid agonists and antagonists have been reviewed. See for example, Zimmerman, D. M.; Leander, J. D. *J. Med. Chem.* 1990, 33, 895; Portoghese, P. S. *J. Med. Chem.* 1992, 35, 1927; Carroll, F. I. *J. Med. Chem.* 2003, 46, 1. The opioid antagonists, nalmefene (1), naltrexone (2), naloxone (3) and naltrexamine (4) are thebaine-derived structures that share a common opiate-type template. μ-Subtype selective opioid antagonists are of considerable current interest as agents for the treatment of obesity (Glass, M. J.; Billington, C. J.; Levine, A. S. *Neuropeptides* 1999, 33, 350) and CNS disorders (Reneric, J. P.; Bouvard, M. P. *CNS Drugs* 1998, 10, 365).

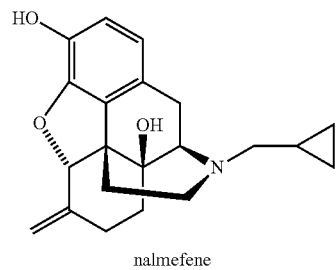
nalmefene

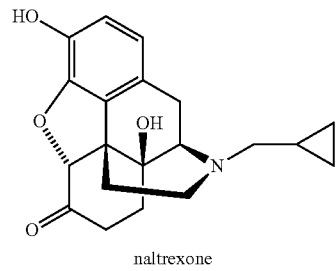
naltrexone

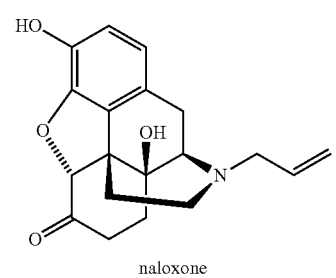
naloxone

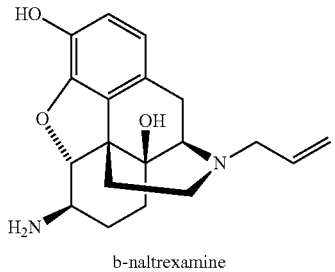
b-naltrexamine

N-Methyl and N-2-phenylethyl substituted opioids tend to show opioid agonist activity whereas N-allyl and N-cyclopropylmethyl substituted analogs tend to show opioid antagonist activity. Any N-attached linker moiety will be larger than methyl. Provided that the linker moiety does not mimic 2-phenylethyl, such linked opioids are expected to behave as opioid antagonists. Therefore, the nitrogen atom of nalmefene and naltrexone (and naloxone) is a suitable site for attachment of a linker moiety. Less SAR information is available with regard to substitution at other sites on these opioids, however, attachment of the linker unit to one or the other of the carbon atoms bearing one or more hydrogen atoms remains an option.

Both nalmefene and naltrexone are potent μ-opioid antagonists. The only structural difference is that nalmefene has a methylene group in place of the ketone oxygen atom in naltrexone. It is thus postulated that significant changes in structure at the ketone oxygen site in naltrexone do not significantly affect antagonist potency. Therefore, a linker may be attached to the methylene group in nalmefene without significant reduction in antagonist potency. Carbonyl derivatives of naloxone are well known and include symmetrical azine (=N—N=), mixed azine (Schmidhammer, H.; Kaspar, F.; Marki, A.; Borsodi, A. *Helv. Chim. Acta* 1994, 77, 999), hydazone (Hahn, E. F.; Itzhak, Y.; Nishimura, S.; Johnson, N.; Pasternak, G. W. *J. Pharm. Exper. Therapeutics* 1985, 235, 846-50), semicarbazone and thiosemicarbazone derivatives (Kolb, V. M.; Koman, A.; Neil, A. Pharmaceutical Res. 1985, 6, 266-71). Naloxazone, the hydrazone of naloxone, is an irreversible, selective and long acting antagonist of the μ-1 subclass of the opioid receptors (Pasternak, G. W.; Hahn, E. F. *J. of Med. Chem.* 1980, 23, 674-6). Certain of the derivatives are potent μ opioid antagonists while others are potent agonists.

Naltrexamine (4) has been linked by attachment of its primary amino group to a wide variety of other molecules producing, for example, a fluorogenic opioid receptor affinity label (Le Bourdonnec, B.; El Kouhen, R.; Lunzer, M. M.; Law, P. Y.; Loh, H. H.; Portoghese, P. S.; *J. Med. Chem.;* 2000; 43; 2489-2492), an extensive series of nonequilibrium opioid agonists and antagonists (Sayre, L. M.; Larson, D. L.; Takemori, A. E.; Portoghese, P. S. *J. Med. Chem.* 1984, 27, 1325), and a series of potent bivalent opioid antagonists (Erez, M.; Takemori, A. E.; Portoghese, P. S. *J. Med. Chem.* 1982, 25, 847-849). Consequently, the primary amino group of naltrexamine constitutes a suitable site for attachment of a linker moiety.

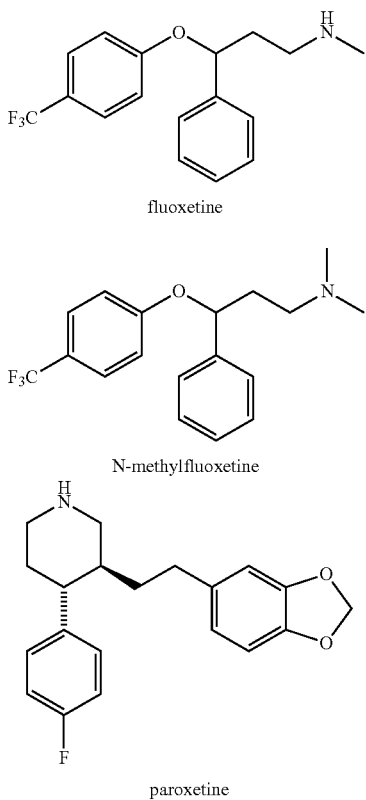

fluoxetine

N-methylfluoxetine paroxetine

A limited SAR for fluoxetine (5) has been published in U.S. Pat. No. 4,214,081, incorporated by reference herein in its entirety. N-Methylfluoxetine (6) shows comparable potency and selectivity to that of fluoxetine toward inhibition of serotonin reuptake. Therefore, attachment of a linker to the nitrogen atom of fluoxetine can result in retention of the potency and selectivity of fluoxetine itself. However, the present disclosure is not limited to the fluoxetine series of SSRIs. It is envisaged that a variety of SSRI molecules such as paroxetine (Dechant, K. L.; Clissold, S. P. *Drugs*, 1991, 41, 225-253) or one or the other of the bivalent SSRIs described by Kozikowski et al. (Tamiz, A. P.; Zhang, J.; Zhang, M.; Wang, C. Z.; Johnson, K. M.; Kozikowski, A. P. *J. Am. Chem. Soc.* 2000, 122, 5393-5394; Tamiz, A. P.; Bandyopadhyay, B. C.; Zhang, J.; Flippen-Anderson, J. L.; Zhang, M.; Wang, C. Z.; Johnson, K. M.; Tella, S.; Kozikowski, A. P. *J. Med. Chem.* 2001, 44, 1615-1622) may also be utilized to construct the heterobivalent therapeutic molecules of this invention.

Examples of linkers reported in the scientific literature include methylene $(CH_2)_n$ linkers (Hussey, S. L.; Muddana, S. S.; Peterson, B. R.; *J. Am. Chem. Soc.* 2003; 125; 3692-3693; Tamiz, A. P.; Bandyopadhyay, B. C.; Zhang, J.; Flippen-Anderson, J. L.; Zhang, M.; Wang, C. Z; Johnson, K. M.; Tellar, S.; Kozikowski, A. P. *J. Med. Chem.* 2001, 44, 1615-1622), oligo ethyleneoxy $O(—CH_2CH_2O—)_n$ units used to link naltrexamine to other opioids, glycine oligomers of the formula $—NH—(COCH_2NH)_nCOCH_2CH_2CO—(NHCH_2CO)_nNH—$ used to link opioid antagonists and agonists together ((a) Portoghese, P. S.; Ronsisvalle, G.; Larson, D. L.; Yim, C. B.; Sayre, L. M.; Takemori, A. E. *Life Sci.* 1982, 31, 1283-1286. (b) Portoghese, P. S.; Larson, D. L.; Sayre, L. M.; Yim, C. B.; Ronsisvalle, G.; Tam, S. W.; Takemori, A. E. *J. Med. Chem.* 1986, 29, 1855-1861), hydrophilic diamines used to link opioid peptides together (Stepinski, J.; Zajaczkowski, I.; Kazem-Bek, D.; Temeriusz, A.; Lipkowski, A. W.; Tam, S. W. Internat. J. of Peptide & Protein Res. 1991, 38, 588-92), rigid double stranded DNA spacers (Paar, J. M.; Harris, N. T.; Holowka, D.; Baird, B. *J. Immunol.* 2002, 169, 856-864) and the biodegradable linker poly (L-lactic acid) (Klok, H.-A.; Hwang, J. J.; Iyer, S. N.; Stupp, S. I. *Macromolecules* 2002, 35, 746-759). The attachment of the tether to the antagonist can result in the antagonist achieving a favorable binding orientation. The linker itself may or may not be biodegradable. The linker may take the form of a prodrug and be tunable for optimal release kinetics of the linked drugs. The linker may be either conformationally flexible throughout its entire length or else a segment of the tether may be designed to be conformationally restricted (Portoghese, P. S.; Ronsisvalle, G.; Larson, D. L.; Takemori, A. E. *J. Med. Chem.* 1986, 29, 1650-1653).

In Scheme 1 below, naltrexone (2) is used in the linking reaction. As a consequence of the Wittig reaction, a double bond replaces the carbonyl group in naltrexone. The net result is fluoxetine linked with a flexible methylene linker to a nalmefene molecule by way of the nalmefene double bond.

Scheme 1

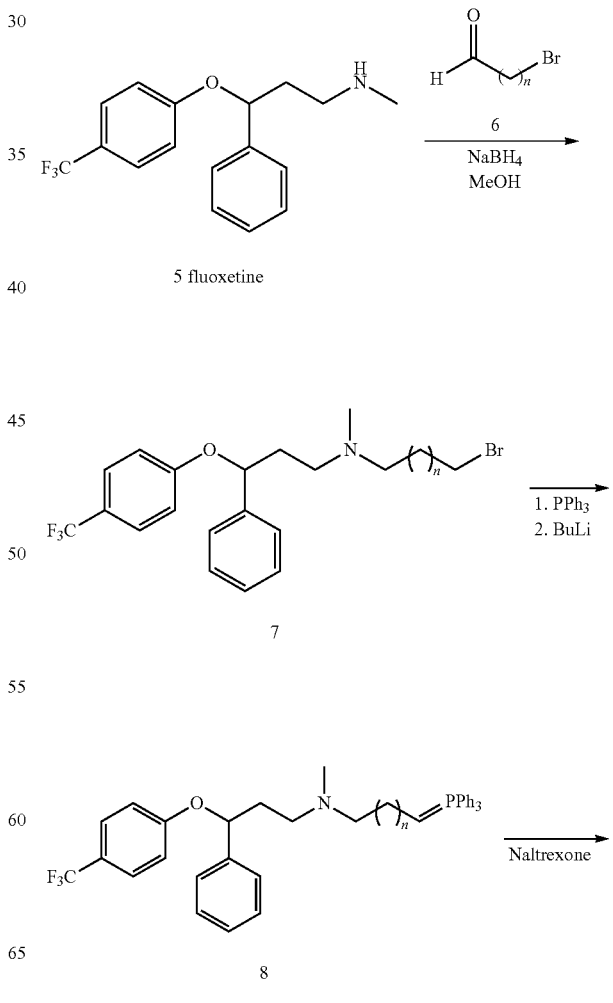

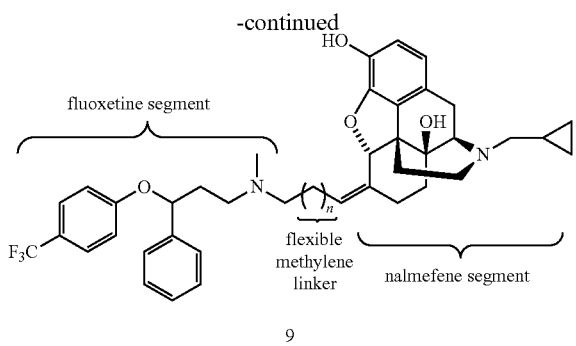

9

Reductive amination of fluoxetine with an ω-bromoaldehyde such as 11-bromoundecanal 6 (n=9) gives bromoamine 7 (n=9), best stored as the hydrobromide salt to prevent an unwanted slow macrocyclization side reaction by way of attack of the free amino group on the carbon bearing the bromine atom. Reaction of 7 with triphenylphosphine gives the intermediate phosphonium salt, which upon rection with butyllithium generates the corresponding ylid 8 (n=9). A Wittig reaction between 8 and the ketone group of naltrexone (2) gives the linked molecule 9 containing a fluoxetine unit coupled to what is now a nalmefene unit. The expected mixture of cis, trans isomers about the newly introduced double bond is separable by standard chromatographic techniques. If racemic fluoxetine is used, then a mixture of two optically active diastereomers of 9 will be produced owing to the fact that a single enantiomer 2 of naltrexone was used. Chemists skilled in the art will recognize that the $(CH_2)_9$ linker may be varied in length and/or contain substituents by beginning with a different bromoaldehyde. Thus, pharmacological properties may be optimized. Molecule 9 is stable under physiological conditions. Opioid antagonist activity will be due to the covalently linked nalmefene unit and not due to free nalmefene released as a result of some cleavage reaction. Similarly, SSRI activity will be due to the covalently linked fluoxetine unit and not due to free fluoxetine released as a result of some cleavage reaction.

An analogous reaction sequence may be used in which the bromoaldehyde is derived from an oligo ethylene glycol as shown in Scheme 2 below. For example, tetraethylene glycol (10 n=2) is converted into bromide 11 (n=2), which is then oxidized under Swern conditions to aldehyde 12 (n=2). Substitution of aldehyde 12 for aldehyde 6 in Scheme 1 will give a series of irreversibly linked molecules in which the linker is more hydrophilic than that in molecules 9. Generation of the ylid in the oligo ethylene glycol series and the subsequent Wittig reaction is performed at reduced temperature to avoid β-elimination of the alkoxy group. If racemic fluoxetine is used, then a mixture of two optically active diastereomers of 13 will be produced owing to the fact that a single enantiomer 2 of naltrexone was used. Chemists skilled in the art will recognize that the $(OCH_2CH_2)_n$ linker may be varied in length by beginning with a different bromoaldehyde 12. Thus, pharmacological properties may be optimized. Molecule 13 is stable under physiological conditions.

Scheme 2

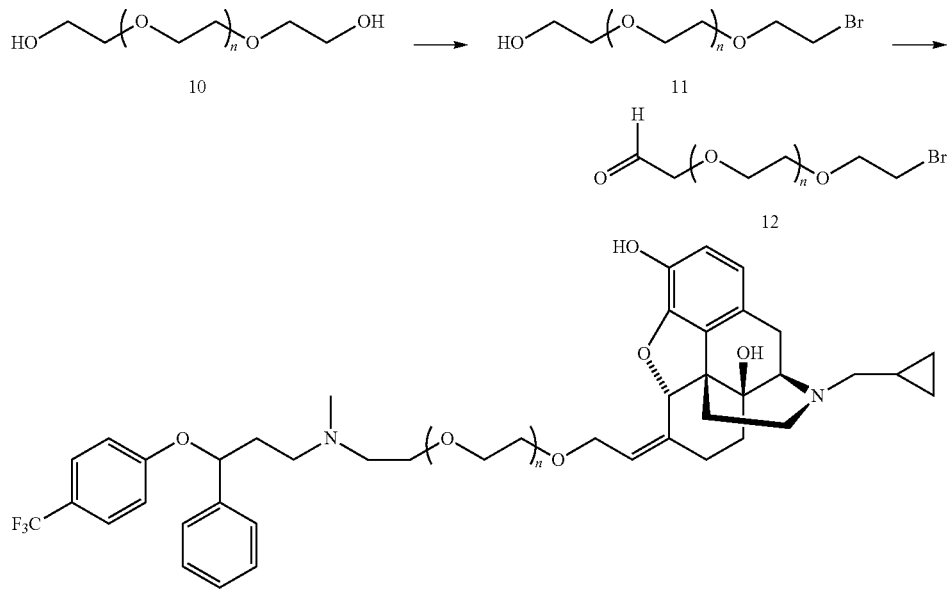

In Scheme 3, another linking method beginning with tetraethylene glycol is illustrated as an example of a variety of oligo ethylene glycols that may be used. Adapting the chemistry of Sashiwa et al. (Sashiwa, H.; Shigemasa, Y.; Roy, R. *Macromolecules* 2000, 33, 6913), tetraethylene glycol may be converted into acetal 14 (n=2) and subsequently into aldehyde 15. Reductive amination of fluoxetine with aldehyde 15 gives the fluoxetine derivative 16. Reduction of azide 16 to amine 17 and then reductive amination with naltrexone gives molecule 18 in which a fluoxetine unit is linked irreversibly by a flexible oligo ethyleneoxy unit to β-naltrexamine (after separation of the α and β isomers). If racemic fluoxetine is used, then a mixture of two optically active diastereomers of 18 will be produced owing to the fact that a single enantiomer 2 of naltrexone was used. Chemists skilled in the art will recognize that the $(OCH_2CH_2)_n$ linker may be varied in length by beginning with a different oligo ethylene glycol 10. Thus, pharmacological properties may be optimized. Molecule 18 should be stable under physiological conditions.

TBDMS protecting group. Chemists skilled in the art will recognize that the $(OCH_2CH_2)_n$ linker may be varied in length by beginning with a different aldehyde azide 15 in the synthesis of 17. Thus, pharmacological properties may be optimized. Molecule 27 should be stable under physiological conditions.

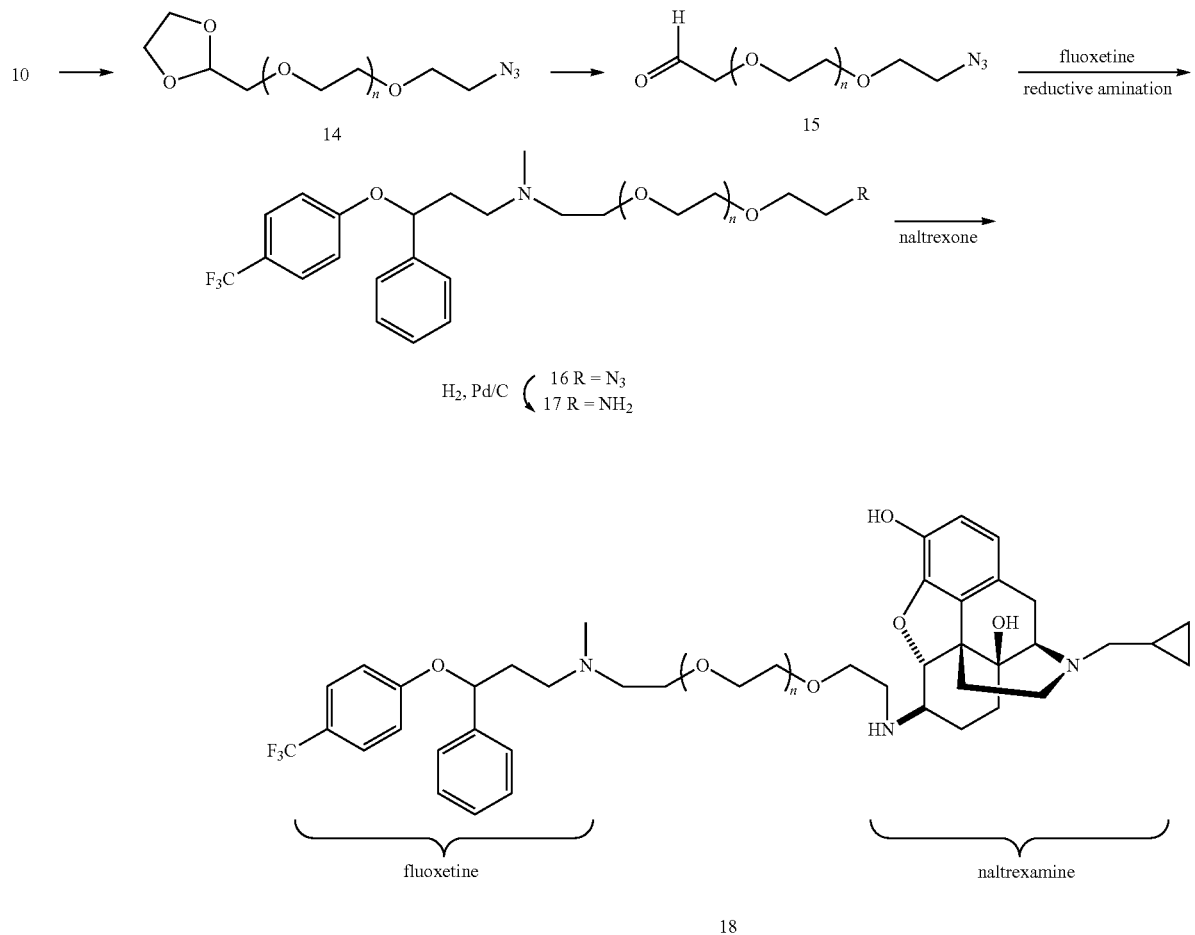

Scheme 4 illustrates a synthetic route to fluoxetine linked to nalmefene by way of the N-cyclopropyl group of nalmefene. The readily available t-butyldimethylsilyl protected noroxymorphone (19) is synthesized from morphine (Ninan, A.; Sainsbury, M. *Tetrahedron* 1992, 48, 6709-16), and then subjected to a reductive amination reaction with the commercially available cyclopropanecarboxaldehyde 20 (Aldrich, largely trans) giving ester 21. Wittig methyleneation gives ester 22, which is hydrolyzed to give acid 23. Activation of acid 23 with an appropriate carbodiimide and then N-acylation of fluoxetine derivative 17 (Scheme 3) gives 25, deprotection of which with $Bu_4NF$ gives the novel molecule 26. Chemists skilled in the art will recognize that the $(OCH_2CH_2)_n$ linker may be varied in length by beginning with a different aldehyde azide 15 in the synthesis of 17. Thus, pharmacological properties may be optimized. Molecule 26 should be stable under physiological conditions.

Alternatively, ester 22 may be reduced to aldehyde 24 using DIBAL at −78° C. Reductive amination of aldehyde 24 with amine 17 gives molecule 27 after removal of the

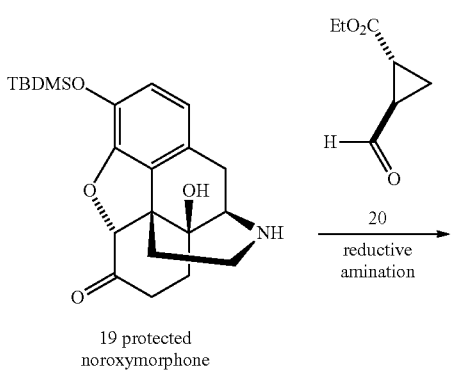

-continued

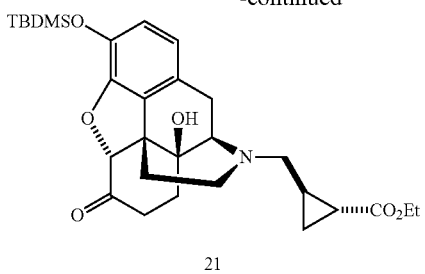

21

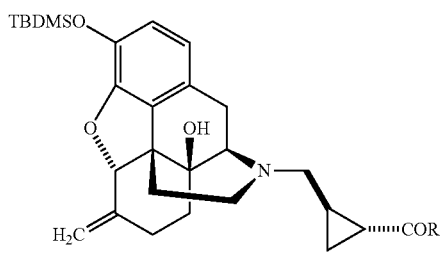

22 R = OEt
23 R = OH
24 R = H

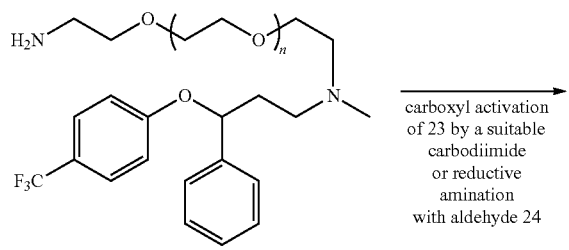

17

-continued

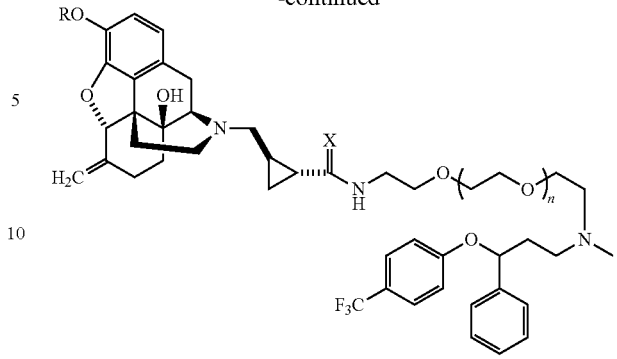

25 R = TBDMS, X = O
26 R = H, X = O
27 R = H, X = H,H

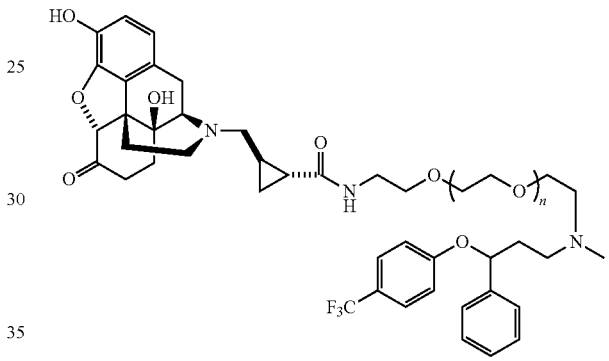

28

If the Wittig methyleneation step is omitted in the above sequence, then an analog of 26, namely ketone 28, is formed in which the methylene group of 26 is replaced by a carbonyl group. The result is a naltrexone unit linked to a fluoxetine unit by way of a flexible, hydrophilic $(CH_2CH_2O)_n$ linker in the form of compound 28. Chemists skilled in the art will recognize that the $(OCH_2CH_2)_n$ linker may be varied in length by beginning with a different aldehyde azide 15 in the synthesis of 17. Thus, pharmacological properties may be optimized. Molecule 28 is stable under physiological conditions.

Scheme 5 illustrates how fluoxetine may be linked to β-naltrexamine using a combination of linkers, namely the flexible glycine-based linkers 29 exploited by Portoghese et al. and the oligo ethylene glycol linkers used in the schemes above. Thus carboxyl activation of 29 with a suitable carbodiimide followed by monocondensation with β-naltrexamine gives amide 30. Reactivation of 30 followed by condensation with amine 17 (Scheme 3) gives molecule 31. Portoghese reports that symmetrical amides derived from linker 29 and β-naltrexamine are effective μ-opioid receptor antagonists. Chemists skilled in the art will recognize that the —NH—$(COCH_2NH)_{n-1}COCH_2CH_2CO$—$(NHCH_2CO)_nNH$— linker may be varied in length by beginning with a different glycine-based linking unit 29 in the synthesis of 30. Thus, pharmacological properties may be optimized. Molecule 31 is stable under physiological conditions.

Scheme 5

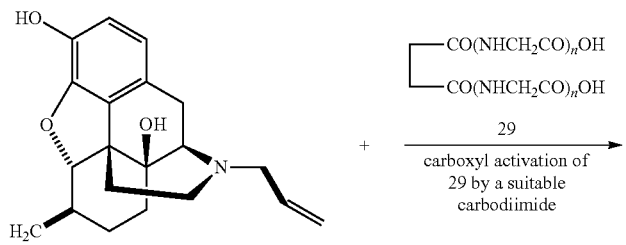

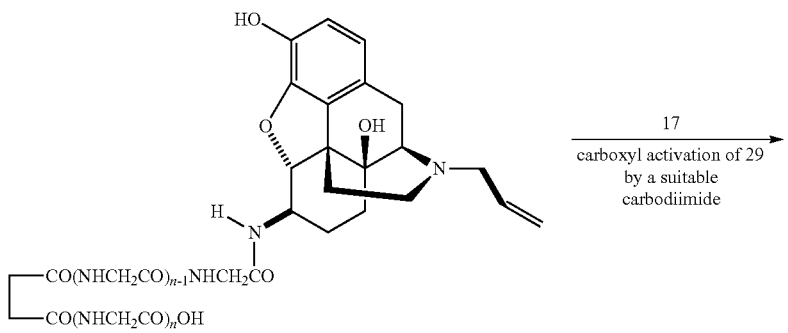

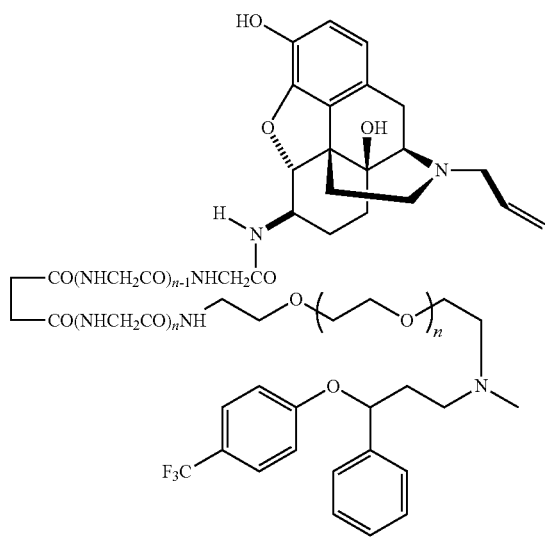

Reaction of bromide 7 (Scheme 1) with Mg in dry THF will give Grignard reagent 32, reaction of which with the carbonyl group of naltrexone gives adduct 33 after separation of the two diastereomers produced at the newly created chiral center. Adduct 33 contains a fluoxetine segment linked to a N-cyclopropylmethyl-normorphine unit by way of a flexible methylene linker. Chemists skilled in the art will recognize that the $(CH_2)_9$ linker may be varied in length by beginning with a different bromoaldehyde for the synthesis of bromide 7. Thus, pharmacological properties may be optimized. Molecule 33 is stable under physiological conditions.

Scheme 6

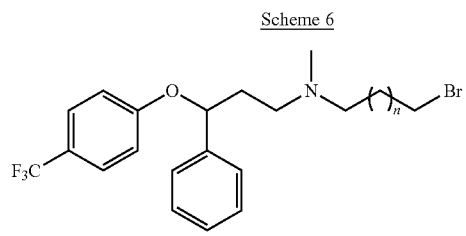

7

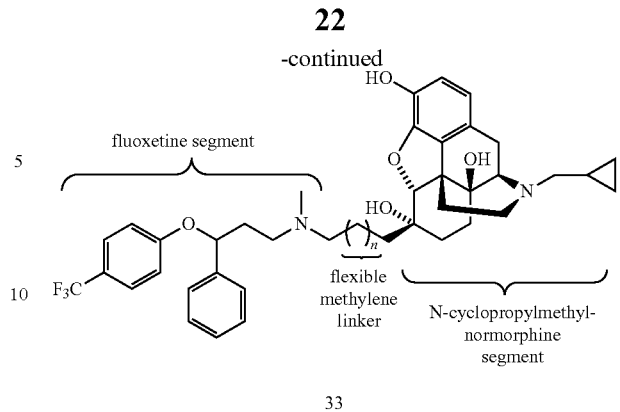

33

Throughout the above schemes, one should be able to employ N-desmethylfluoxetine (34), or any other derivative of fluoxetine, in place of fluoxetine. The resulting linked fluoxetine unit is identical to that of fluoxetine itself except that the methyl group of fluoxetine is replaced by a longer chain that is part of the linker. When necessary due to the use of strongly basic reagents or when chemoselectivity toward a primary amino group elsewhere in the molecule is required, one may protect the intermediate fluoxetine secondary amino group by use of the N-[2-(trimethylsilyl)ethoxy]methyl (SEM) group (Zeng, Z.; Zimmerman, S. C. *Tetrahedron Lett.* 1988, 29, 5123) as illustrated in Scheme 7.

Scheme 7

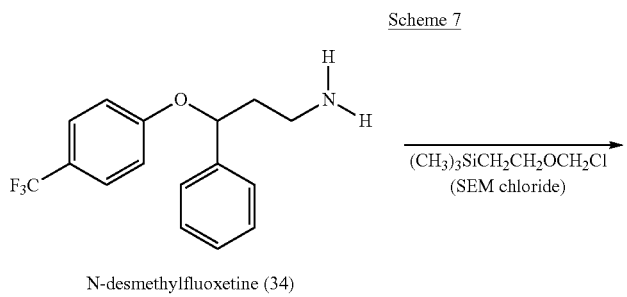

N-desmethylfluoxetine (34)

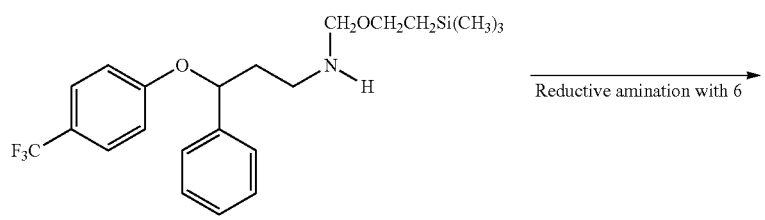

35

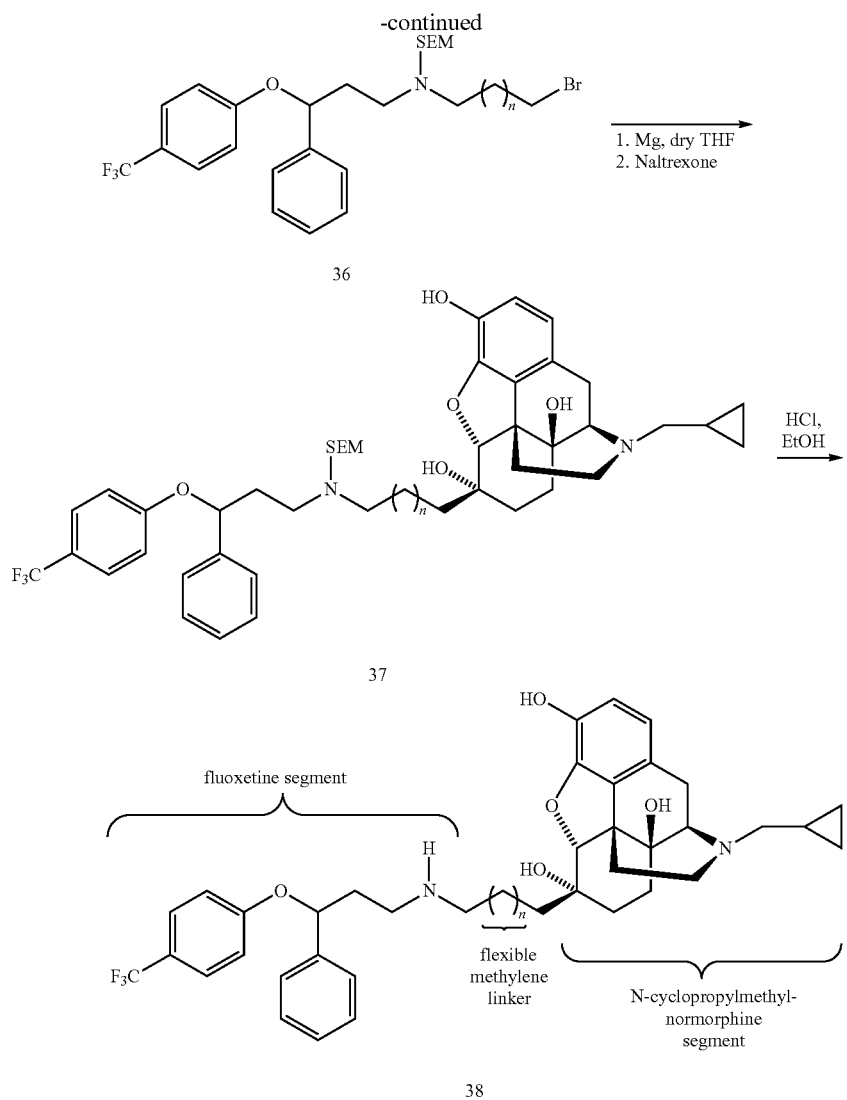

In another aspect, the invention relates to a pharmaceutical composition comprising a combination of an opioid antagonist and a compound that causes increased agonism of a melanocortin 3 receptor (MC3-R) or a melanocortin 4 receptor (MC4-R) compared to normal physiological conditions, as described above, or comprising a linked molecule, as described herein, and a physiologically acceptable carrier, diluent, or excipient, or a combination thereof.

The term "pharmaceutical composition" refers to a mixture of a compound of the invention with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the compound in a local rather than systemic manner, for example, via injection of the compound directly in the renal or cardiac area, often in a depot or sustained release formulation. Furthermore, one may administer the drug in a targeted drug delivery system, for example, in a liposome coated with a tissue-specific antibody. The liposomes will be targeted to and taken up selectively by the organ.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by mixing one or more solid excipient with pharmaceutical combination of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Many of the compounds used in the pharmaceutical combinations of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acid or base forms.

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", Ch. 1 p. 1). Typically, the dose range of the composition administered to the patient can be from about 0.5 to 1000 mg/kg of the patient's body weight. The dosage may be a single one or a series of two or more given in the course of one or more days, as is needed by the patient. Note that for almost all of the specific compounds mentioned in the present disclosure, human dosages for treatment of at least some condition have been established. Thus, in most instances, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

Although the exact dosage will be determined on a drug-by-drug basis, in most cases, some generalizations regarding the dosage can be made. The daily dosage regimen for an adult human patient may be, for example, an oral dose of between 0.1 mg and 500 mg of each ingredient, preferably between 1 mg and 250 mg, e.g. 5 to 200 mg or an intravenous, subcutaneous, or intramuscular dose of each ingredient between 0.01 mg and 100 mg, preferably between 0.1 mg and 60 mg, e.g. 1 to 40 mg of each ingredient of the pharmaceutical compositions of the present invention or a pharmaceutically acceptable salt thereof calculated as the free base, the composition being administered 1 to 4 times per day. Alternatively the compositions of the invention may be administered by continuous intravenous infusion, preferably at a dose of each ingredient up to 400 mg per day. Thus, the total daily dosage by oral administration of each ingredient will typically be in the range 1 to 2000 mg and the total daily dosage by parenteral administration will typically be in the range 0.1 to 400 mg. Suitably the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

It will be understood by those of skill in the art that numerous and various modifications can be made without departing from the spirit of the present invention. Therefore, it should be clearly understood that the forms of the present invention are illustrative only and are not intended to limit the scope of the present invention.

Some Embodiments of the Invention

Some of the embodiments of the present invention are as follows:

In the first embodiment, the invention relates to a composition for affecting weight loss comprising a first compound and a second compound, wherein said first compound is an opioid antagonist and said second compound causes increased agonism of a melanocortin 3 receptor (MC3-R) or a melanocortin 4 receptor (MC4-R) compared to normal physiological conditions.

In the second embodiment, the invention relates to the composition of the first embodiment, wherein said opioid antagonist antagonizes an opioid receptor in a mammal.

In the third embodiment, the invention relates to the composition of the second embodiment, wherein said opioid receptor is selected from a μ-opioid receptor (MOP-R), a κ-opioid receptor, and a δ-opioid receptor.

In the fourth embodiment, the invention relates to the composition of the second embodiment, wherein said opioid antagonist antagonizes a μ-opioid receptor (MOP-R) in a mammal.

In the fifth embodiment, the invention relates to the composition of the first embodiment, wherein said opioid antagonist is selected from the group consisting of alvimopan, norbinaltorphimine, nalmefene, naloxone, naltrexone, methylnaltrexone, and nalorphine, and pharmaceutically acceptable salts or prodrugs thereof.

In the sixth embodiment, the invention relates to the composition of the first embodiment, wherein said opioid antagonist is a partial opioid agonist.

In the seventh embodiment, the invention relates to the composition of the sixth embodiment, wherein said partial opioid agonist is selected from the group consisting of pentacozine, buprenorphine, nalorphine, propiram, and lofexidine.

In the eighth embodiment, the invention relates to the composition of the first embodiment, wherein said second compound triggers the release of α-melanocyte stimulating hormone (α-MSH).

In the ninth embodiment, the invention relates to the composition of the eighth embodiment, wherein said second compound increases the extracellular serotonin concentrations in the hypothalamus.

In the tenth embodiment, the invention relates to the composition of the ninth embodiment, wherein said second compound is selected from the group consisting of a selective serotonin reuptake inhibitor (SSRI), a serotonin 2C agonist, and a serotonin 1B agonist.

In the eleventh embodiment, the invention relates to the composition of the tenth embodiment, wherein said second compound is selected from the group consisting of fluoxetine, fluvoxamine, sertraline, paroxetine, citalopram, escitalopram, sibutramine, duloxetine, and venlafaxine, and pharmaceutically acceptable salts or prodrugs thereof.

In the twelfth embodiment, the invention relates to the composition of the first embodiment, wherein said second compound suppresses the expression of the AgRP gene or the production or release of agouti-related protein (AgRP).

In the thirteenth embodiment, the invention relates to the composition of the first embodiment, wherein said second compound suppresses the activity of neurons that express AgRP.

In the fourteenth embodiment, the invention relates to the composition of the first embodiment, wherein said second compound suppresses the expression of the NPY gene or the production or release of neuropeptide Y (NPY).

In the fifteenth embodiment, the invention relates to the composition of the first embodiment, wherein said second compound suppresses the activity of neurons that express NPY.

In the sixteenth embodiment, the invention relates to the composition of the first embodiment, wherein said second compound is selected from the group consisting of NPY Y1 receptor antagonists, ghrelin antagonists, and leptin.

In the seventeenth embodiment, the invention relates to the composition of the first embodiment, wherein said second compound agonizes NPY Y2 receptor.

In the eighteenth embodiment, the invention relates to the composition of the first embodiment, wherein said second compound is selected from the group consisting of a γ-amino butyric acid (GABA) inhibitor, a GABA receptor antagonist, and a GABA channel antagonist.

In the nineteenth embodiment, the invention relates to the composition of the eighteenth embodiment, wherein said GABA inhibitor is a 5-HT1b agonist, which may be selected from sumatriptan, almotriptan, naratriptan, frovatriptan, rizatriptan, zomitriptan, and elitriptan.

In the twentieth embodiment, the invention relates to the composition of the eighteenth embodiment, wherein said GABA inhibitor suppresses the expression of the AgRP gene.

In the twenty first embodiment, the invention relates to the composition of the eighteenth embodiment, wherein said GABA inhibitor suppresses the production or release of AgRP.

In the twenty second embodiment, the invention relates to the composition of the eighteenth embodiment, wherein said GABA inhibitor increases the expression of the POMC gene.

In the twenty third embodiment, the invention relates to the composition of the eighteenth embodiment, wherein said GABA inhibitor increases the production or release of α-MSH from pro-opiomelanocortin (POMC) neurons.

In the twenty fourth embodiment, the invention relates to the composition of the eighteenth embodiment, wherein said GABA inhibitor increases the activity of POMC expressing neurons.

In the twenty fifth embodiment, the invention relates to the composition of the eighteenth embodiment, wherein the GABA inhibitor is topiramate.

In the twenty sixth embodiment, the invention relates to the composition of the first embodiment, wherein said second compound is a dopamine reuptake inhibitor.

In the twenty seventh embodiment, the invention relates to the composition of the twenty sixth embodiment, wherein said dopamine reuptake inhibitor is phentermine.

In the twenty eighth embodiment, the invention relates to the composition of the first embodiment, wherein said second compound is a norepinephrine reuptake inhibitor.

In the twenty ninth embodiment, the invention relates to the composition of the twenty eighth embodiment, wherein said norepinephrine reuptake inhibitor is selected from bupropion, thionisoxetine, and reboxetine.

In the thirtieth embodiment, the invention relates to the composition of the first embodiment, wherein said second compound is a dopamine agonist.

In the thirty first embodiment, the invention relates to the composition of the thirtieth embodiment, wherein said dopamine agonist is selected from the group consisting of cabergoline, amantadine, lisuride, pergolide, ropinirole, pramipexole, and bromocriptine.

In the thirty second embodiment, the invention relates to the composition of the first embodiment, wherein said second compound is a norepinephrine releaser.

In the thirty third embodiment, the invention relates to the composition of the thirty second embodiment, wherein said norepinephrine releaser is diethylpropion.

In the thirty fourth embodiment, the invention relates to the composition of the first embodiment, wherein said second compound is a combination of a dopamine reuptake inhibitor and a norepinephrine reuptake inhibitor.

In the thirty fifth embodiment, the invention relates to the composition of the thirty fourth embodiment, wherein said second compound is selected from bupropion and mazindol.

In the thirty sixth embodiment, the invention relates to the composition of the first embodiment, wherein said second compound is a combination of a SSRI and a norepinephrine reuptake inhibitor.

In the thirty seventh embodiment, the invention relates to the composition of the thirty sixth embodiment, wherein said second compound is selected from sibutramine, venlafaxine, and duloxetine.

In the thirty eighth embodiment, the invention relates to the composition of the first embodiment, wherein said first compound is naltrexone and said second compound is fluoxetine.

In the thirty ninth embodiment, the invention relates to the composition of the thirty eighth embodiment, wherein the naltrexone is in a time-release formulation whereas the fluoxetine is in an immediate release formulation.

In the fortieth embodiment, the invention relates to a method of affecting weight loss, comprising identifying an individual in need thereof and treating that individual to antagonize opioid receptor activity and to enhance α-MSH activity.

In the forty first embodiment, the invention relates to the method of the fortieth embodiment, wherein said individual has a body mass index greater than 25.

In the forty second embodiment, the invention relates to the method of the fortieth embodiment, wherein opioid receptor activity is antagonized by administering an opioid receptor antagonist.

In the forty third embodiment, the invention relates to the method of the forty second embodiment, wherein the opioid receptor antagonist is a MOP receptor antagonist.

In the forty fourth embodiment, the invention relates to the method of the fortieth embodiment, wherein the opioid receptor antagonist is selected from alvimopan, norbinaltorphimine, nalmefene, naloxone, naltrexone, methylnaltrexone, and nalorphine, and pharmaceutically acceptable salts or prodrugs thereof.

In the forty fifth embodiment, the invention relates to the method of the forty second embodiment, wherein said opioid receptor antagonist is a partial opioid agonist.

In the forty sixth embodiment, the invention relates to the method of the forty fifth embodiment, wherein said partial opioid agonist is selected from the group consisting of pentacozine, buprenorphine, nalorphine, propiram, and lofexidine.

In the forty seventh embodiment, the invention relates to the method of the fortieth embodiment through the forty fifth embodiment, wherein α-MSH activity is enhanced by administering a compound, wherein said compound triggers release of α-MSH or increases the activity of neurons that express α-MSH.

In the forty eighth embodiment, the invention relates to the method of the forty seventh embodiment, wherein said compound is a selective serotonin reuptake inhibitor (SSRI) or a specific 5-HT receptor agonist.

In the forty ninth embodiment, the invention relates to the method of the forty eighth embodiment, wherein said 5-HT receptor is selected from 5-HT1b receptor and 5-HT2c receptor.

In the fiftieth embodiment, the invention relates to the method of the forty eighth embodiment, wherein said SSRI is selected from fluoxetine, fluvoxamine, sertraline, paroxetine, citalopram, escitalopram, sibutramine, duloxetine, and venlafaxine, and pharmaceutically acceptable salts or prodrugs thereof.

In the fifty first embodiment, the invention relates to the method of the forty seventh embodiment, wherein said compound is a γ-amino butyric acid (GABA) inhibitor.

In the fifty second embodiment, the invention relates to the method of the fifty first embodiment, wherein said GABA inhibitor is a 5-HT1b receptor agonist.

In the fifty third embodiment, the invention relates to the method of the fifty first embodiment, wherein said GABA inhibitor suppresses the expression of the AgRP gene.

In the fifty fourth embodiment, the invention relates to the method of the fifty first embodiment, wherein said GABA inhibitor suppresses the production or release of AgRP.

In the fifty fifth embodiment, the invention relates to the method of the forty eighth embodiment, wherein said 5-HT agonists inhibits the NPY/AgRP/GABA neurons.

In the fifty sixth embodiment, the invention relates to the method of the fifty first embodiment, wherein said GABA inhibitor suppresses the activity of neurons that express AgRP.

In the fifty seventh embodiment, the invention relates to the method of the fifty first embodiment, wherein said GABA inhibitor is topiramate.

In the fifty eighth embodiment, the invention relates to the method of the forty seventh embodiment, wherein said compound is selected from the group consisting of a dopamine reuptake inhibitor, a norepinephrine reuptake inhibitor, a dopamine agonist, a norepinephrine releaser, a combination of a dopamine reuptake inhibitor and a norepinephrine reuptake inhibitor, and a combination of a SSRI and a norepinephrine reuptake inhibitor.

In the fifty ninth embodiment, the invention relates to the method of the fifty eighth embodiment, wherein said compound is not phentermine.

In the sixtieth embodiment, the invention relates to the method of the fortieth embodiment, with the proviso that the individual is not suffering from Prader-Willi syndrome.

In the sixty first embodiment, the invention relates to the method of the fortieth embodiment, with the proviso that if the opioid receptor is antagonized using naltrexone, then release of α-MSH is not stimulated with fluoxetine.

In the sixty second embodiment, the invention relates to the method of the fortieth embodiment, wherein said treating step comprises administering to said individual a first compound and a second compound, wherein said first compound is an opioid antagonist and said second compound enhances α-MSH activity.

In the sixty third embodiment, the invention relates to the method of the sixty second embodiment, wherein said first compound and said second compound are administered nearly simultaneously.

In the sixty fourth embodiment, the invention relates to the method of the sixty third embodiment, wherein said first compound is administered prior to said second compound.

In the sixty fifth embodiment, the invention relates to the method of the sixty fourth embodiment, wherein said first compound is administered subsequent to said second compound.

In the sixty sixth embodiment, the invention relates to a method of increasing satiety in an individual comprising identifying an individual in need thereof and treating that individual to antagonize opioid receptor activity and to enhance α-MSH activity.

In the sixty seventh embodiment, the invention relates to the method of the sixty sixth embodiment, wherein said treating step comprises administering to said individual a first compound and a second compound, wherein said first compound is an opioid antagonist and said second compound enhances α-MSH activity.

In the sixty eighth embodiment, the invention relates to the method of the sixty seventh embodiment, wherein said first compound and said second compound are administered nearly simultaneously.

In the sixty ninth embodiment, the invention relates to the method of the sixty seventh embodiment, wherein said first compound is administered prior to said second compound.

In the seventieth embodiment, the invention relates to the method of the sixty seventh embodiment, wherein said first compound is administered subsequent to said second compound.

In the seventy first embodiment, the invention relates to a method of increasing energy expenditure in an individual comprising identifying an individual in need thereof and treating that individual to antagonize opioid receptor activity and to enhance α-MSH activity.

In the seventy second embodiment, the invention relates to the method of the seventy first embodiment, wherein said treating step comprises administering to said individual a first compound and a second compound, wherein said first compound is an opioid antagonist and said second compound enhances α-MSH activity.

In the seventy third embodiment, the invention relates to the method of the seventy second embodiment, wherein said first compound and said second compound are administered nearly simultaneously.

In the seventy fourth embodiment, the invention relates to the method of the seventy second embodiment, wherein said first compound is administered prior to said second compound.

In the seventy fifth embodiment, the invention relates to the method of the seventy second embodiment, wherein said first compound is administered subsequent to said second compound.

In the seventy sixth embodiment, the invention relates to a method of suppressing the appetite of an individual comprising identifying an individual in need thereof and treating that individual to antagonize opioid receptor activity and to enhance α-MSH activity.

In the seventy seventh embodiment, the invention relates to the method of the seventy sixth embodiment, wherein said treating step comprises administering to said individual a first compound and a second compound, wherein said first compound is an opioid antagonist and said second compound enhances α-MSH activity.

In the seventy eighth embodiment, the invention relates to the method of the seventy seventh embodiment, wherein said first compound and said second compound are administered nearly simultaneously.

In the seventy ninth embodiment, the invention relates to the method of the seventy seventh embodiment, wherein said first compound is administered prior to said second compound.

In the eightieth embodiment, the invention relates to the method of the seventy seventh embodiment, wherein said first compound is administered subsequent to said second compound.

In the eighty first embodiment, the invention relates to a method of affecting weight loss in an individual comprising identifying an individual in need thereof and treating that individual with a combination of naltrexone and fluoxetine, provided that the individual does not suffer from Prader-Willi syndrome or binge eating disorder.

In the eighty second embodiment, the invention relates to the method of the eighty first embodiment, wherein the individual has a BMI greater than 30.

In the eighty third embodiment, the invention relates to the method of the eighty first embodiment, wherein the individual has a BMI greater than 25.

In the eighty fourth embodiment, the invention relates to the method of the eighty first embodiment, wherein the naltrexone is in a time-release formulation whereas the fluoxetine is in an immediate release formulation.

In the eighty fifth embodiment, the invention relates to the method of the eighty fourth embodiment, wherein the plasma concentration level of both naltrexone and fluoxetine follow a similar concentration profile.

In the eighty sixth embodiment, the invention relates to the method of the eighty fourth embodiment, wherein the naltrexone and the fluoxetine are administered substantially simultaneously.

In the eighty seventh embodiment, the invention relates to the method of the eighty fourth embodiment, wherein the naltrexone is administered prior to the fluoxetine.

In the eighty eighth embodiment, the invention relates to the method of the eighty fourth embodiment, wherein the naltrexone is administered subsequent to the fluoxetine.

EXAMPLES

The examples below are non-limiting and are merely representative of various aspects of the invention.

Example 1: Combination of Fluoxetine and Naltrexone

Individuals having a BMI of greater than 25 are identified. Each individual is instructed to take one 20 mg tablet of fluoxetine (PROZAC®) on a daily basis, in addition to one 50 mg tablet of naltrexone on a daily basis.

The individuals are monitored for a period of months. It is recommended that the dosage be adjusted so that each individual loses weight at a rate of 10% of initial weight every 6 months. However, the rate of weigh loss for each individual may be adjusted by the treating physician based on the individual's particular needs.

If the initial dosage is not effective, then the fluoxetine dosage can be increased by 20 mg per day, though never exceeding 80 mg total per day. If the initial dosage results in a more rapid weight loss than the above rate, the dosage of each of fluoxetine or naltrexone can be reduced.

Fluoxetine has a physiological half life of about 9 hours, whereas that of naltrexone is about 1.5 hours. Thus, in some cases, it is beneficial to administer one dose of fluoxetine per day in conjunction with two or three or more doses of naltrexone throughout the day. Naltrexone may also be in a time-release formulation where the dose is administered once a day, but naltrexone gradually enters the blood stream throughout the day, or in the course of a 12 hour period.

Example 2: Combination of Fluoxetine and Nalmefene

Individuals having a BMI of greater than 25 are identified. Each individual is instructed to take one 20 mg tablet of fluoxetine (PROZAC®) on a daily basis. In addition, each individual is injected with 1 mL of a solution of 100 µg of nalmefene in 1 mL of saline, intravenously, intramuscularly, or subcutaneously.

The individuals are monitored for a period of months. It is recommended that the dosage be adjusted so that each individual loses weight at a rate of 10% of initial weight every 6 months. However, the rate of weigh loss for each individual may be adjusted by the treating physician based on the individual's particular needs.

If the initial dosage is not effective, then the fluoxetine dosage can be increased by 20 mg per day, though never exceeding 80 mg total per day. In addition, the dosage of nalmefene may be increased up to 2 mL of a solution of 1 mg of nalmefene in 1 mL of saline. If the initial dosage results in a more rapid weight loss than the above rate, the dosage of each of fluoxetine or nalmefene can be reduced.

Example 3: Combination of Fluoxetine and Naloxone

Individuals having a BMI of greater than 25 are identified. Each individual is instructed to take one 20 mg tablet of fluoxetine (PROZAC®) on a daily basis. In addition, each individual is injected with 1 mL of a solution of 400 µg of naloxone in 1 mL of saline, intravenously, intramuscularly, or subcutaneously.

The individuals are monitored for a period of months. It is recommended that the dosage be adjusted so that each individual loses weight at a rate of 10% of initial weight every 6 months. However, the rate of weigh loss for each individual may be adjusted by the treating physician based on the individual's particular needs.

If the initial dosage is not effective, then the fluoxetine dosage can be increased by 20 mg per day, though never exceeding 80 mg total per day. If the initial dosage results in a more rapid weight loss than the above rate, the dosage of each of fluoxetine or nalmefene can be reduced.

Example 4: Combination of Opioid Antagonist and Sibutramine

Individuals having a BMI of greater than 25 are identified. Each individual is instructed to take nalmefene, naltrexone, or naloxone in the dosage set forth in Examples 1-3. In addition, each individual is instructed to take 10 mg of sibutramine orally once a day.

The individuals are monitored for a period of months. It is recommended that the dosage be adjusted so that each individual loses weight at a rate of 10% of initial weight every 6 months. However, the rate of weigh loss for each individual may be adjusted by the treating physician based on the individual's particular needs.

If the initial dosage is not effective, then the sibutramine dosage can be increased 15 mg per day. Dosages of sibutramine in excess of 15 mg per day are not recommended. If the initial dosage results in a more rapid weight loss than the above rate, the dosage of each of sibutramine, nalmefene, naltrexone, or naloxone can be reduced.

Example 5: Combination of Opioid Antagonist and Bupropion

Individuals having a BMI of greater than 25 are identified. Each individual is instructed to take nalmefene, naltrexone, or naloxone in the dosage set forth in Examples 1-3. In addition, each individual is instructed to take bupropion. The usual adult does is 300 mg per day, given three times daily. Dosing should begin at 200 mg per day, given as 100 mg twice daily. Based on clinical response, this dose may be increased to 300 mg per day, given as 100 mg three times daily. No single dose is to exceed 150 mg.

The individuals are monitored for a period of months. It is recommended that the dosage be adjusted so that each individual loses weight at a rate of 10% of initial weight every 6 months. However, the rate of weigh loss for each individual may be adjusted by the treating physician based on the individual's particular needs.

Example 6: Combination of Opioid Antagonist and Phentermine

Individuals having a BMI of greater than 25 are identified. Each individual is instructed to take nalmefene, naltrexone, or naloxone in the dosage set forth in Examples 1-3. In addition, each individual is instructed to take 37.5 mg of phentermine orally once a day.

The individuals are monitored for a period of months. It is recommended that the dosage be adjusted so that each individual loses weight at a rate of 10% of initial weight every 6 months. However, the rate of weigh loss for each individual may be adjusted by the treating physician based on the individual's particular needs.

Example 7: Combinations with Naltrexone

In a multicenter, randomized, blinded, placebo-controlled clinical trial with 6 groups, the following drug combinations are tested:

Group 1: Fluoxetine 60 mg po QD plus Naltrexone 50 mg po QD

Group 2: Fluoxetine 60 mg po QD plus N-placebo po QD

Group 3: Bupropion-SR 150 mg po BID plus Naltrexone 50 mg po QD

Group 4: Bupropion-SR 150 mg po BID plus N-placebo po QD

Group 5: P-placebo po BID plus Naltrexone 50 mg po QD

Group 6: P-placebo po BID plus N-placebo po QD

In any of the above groups, the dosage of fluoxetine may be in the range between 6 mg and 60 mg, for example, 6 mg, 10 mg, 12 mg, 18 mg, 20 mg, 24 mg, 30 mg, 36 mg, 40 mg, 42 mg, 45 mg, 48 mg, 54 mg, and 60 mg. Bupropion may be administered in doses in the range between 30 mg and 300 mg, for example, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, and 300 mg. Naltrexone may be administered in doses in the range between 5 mg and 50 mg, for example, 5 mg, 10 mg, 15 mg, 20 mg, 25 mg, 30 mg, 35 mg, 40 mg, 45 mg, and 50 mg.

Subjects are evaluated as out-patients during this study. All subjects in this trial receive diet instruction, behavior modification advice and instruction to increase their activity, a regimen shown to give weight loss. Subjects are randomized to receive study drugs in various combinations.

Subjects in groups 5 and 6 cross-over to treatment with fluoxetine plus naltrexone or bupropion SR plus naltrexone after week 16 for the extension treatment period which provide additional data on safety of the combination therapies.

The primary endpoint is percent and absolute change from baseline in body weight at 16 weeks. Secondary endpoints include weight loss at 24, 36, and 48 weeks, number and proportion of subjects who achieve at least a 5% weight loss and a 10% weight loss (responder analysis), changes in obesity-associated cardiovascular risk factors (total cholesterol, LDL cholesterol, HDL cholesterol, triglycerides, glucose and insulin) and waist circumference, and safety and tolerability. Adverse events, laboratory parameters, vital signs, and the Hospital Anxiety and Depression (HAD) Scale are used to monitor safety and tolerability.

Example 8: Dose-Response Experiments

Seventy, four week old, male C57/B16J⁻ mice (Jackson Laboratory), 22-30 g were sham injected daily with 0.1 mL 0.9% saline (pH 7.4) for 1 week prior to the experiments. Animals were weighed and randomized to 1 of 7 weight-matched dose groups (0, 1.5, 3, 5.5, 10, 18, and 30 mg/kg; n=10/group for fluoxetine; 0, 1.5, 3, 5.5, 10, 18, and 30 mg/kg; n=3/group for naltrexone) the day before experiments began. Food was removed between 4:30-5:30 pm the day before the experiment. Animals received a 0.3 mL bolus (fluoxetine) or 0.1 mL bolus (naltrexone) intraperitoneal injection between 9-10:30 am, and food was provided immediately following injection. 3 animals/group received injections on each testing day (i.e., 3 runs of 3/group; 1 run of 1/group). Food was weighed 1, 2, 4, 8, and 24 h post-injection. Cumulative food intake±SEM was calculated and analyzed using Prizm. The SEM for these numbers was found to be between 0.0041 and 0.26. Doses were log transformed and fit to a sigmoidal curve, food intake was expressed as a proportion of the food intake in saline treated animals. From the curve, the $EC_{50}$ at each time point for each drug was determined.

Similar procedures as described above were followed using fluvoxamine and nalmefene, and bupropion and naltrexone.

The results are set forth in the table below.

|  | Hour 1 MEAN | Hour 2 MEAN | Hour 4 MEAN | Hour 8 MEAN | Hour 24 MEAN |
|---|---|---|---|---|---|
| Saline | 1.00 | 1.00 | 1.00 | 1.00 | 1.00 |
| Fluvoxamine | 0.77 | 0.85 | 0.95 | 0.91 | 0.92 |
| Nalmefene | 0.0083 | 0.11 | 0.57 | 0.81 | 0.98 |
| Fluvoxamine + Nalmefene | 0.0041 | 0.019 | 0.42 | 0.79 | 0.99 |
| Bupropion | 0.32 | 0.64 | 0.97 | 0.96 | 0.99 |
| Naltrexone | 0.41 | 0.77 | 0.99 | 1.1 | 0.98 |
| Naltrexone + Bupropion | 0.042 | 0.34 | 0.89 | 0.97 | 0.95 |
| Naltrexone | 0.30 | 0.56 | 0.83 | 0.98 | 1.01 |
| Fluoxetine | 0.36 | 0.57 | 0.68 | 0.76 | 1.05 |
| Naltrexone + Fluoxetine | 0.070 | 0.26 | 0.72 | 0.95 | 1.04 |

Example 9: Electrophysiology Data

To test the hypothesis that drugs selectively activate POMC neurons, we used a strain of transgenic mice expressing green fluorescent protein (EGFP, Clontech), under the transcriptional control of mouse Pomc genomic sequences that include a region located between −13 kb and −2 kb required for accurate neuronal expression Bright green fluorescence (509 nm) was seen in the two CNS regions where POMC is produced: the ARC and the nucleus of the solitary tract. Under ultraviolet (450-480 nm) excitation, POMC neurons were clearly distinguished from adjacent, non-fluorescent neurons visualized under infrared optics.

200 μm thick coronal slices were cut from the ARC of four-week old male POMC-EGFP mice. Slices were maintained in Krebs solution (NaCl (126 mM), KCl (2.5 mM), $MgCl_2$ 91.2 mM), $CaCl_2.2H_2O$ (2.4 mM), $NaH_2PO_4.H_2O$ (1.2 mM), $NaHCO_3$ (21.4 mM), glucose (11.1 mM)) at 35° C. and saturated with 95% $O_2$ and 5% $CO_2$ for 1 hr prior to recordings. Recordings were made in Krebs at 35° C. Slices were visualized on an Axioskop FS2 plus (Zeiss) through standard infra red optics and using epifluorescence through a FITC (longpass) filter set. POMC-EGFP neurons in hypothalamic slices had a resting membrane potential of −40 to −45 mV and exhibited frequent spontaneous action potentials. Cell-attached recordings were made from fluorescent neurons using an Axopatch 200B amplifier (Axon Instruments) and Clampex 8 (Axon Instruments). Action potentials frequencies were determined using an event detection program (Mini Analysis; Synaptosoft Inc., Decatur, Ga.). Drugs were applied to the bath for 3 min.

Data were analyzed by determining the average firing rate for 500 sec prior to drug addition, and analyzing treatments relative to this frequency (that is, firing rates were normalized to the pre-treatment frequency). The ratio's listed for the combinations are the ratio of the effect of naltrexone in combination with the POMC activator, relative to naltrexone alone (that is the extra effectiveness that naltrexone conferred to the POMC activator). Also listed are the mean effects of the drugs alone.

| Fenfluramine | 2X increase (n = 6) |
| Fenfluramine + Naltrexone | 5.2X (n = 8) |
| Fluoxetine | 3X (n = 1) |
| Fluoxetine + Naltrexone | 1.2X (n = 1) |
| Dopamine | 11X (n = 9) |
| Dopamine + Naltrexone | 1.5X (n = 3) |

Naltrexone alone has a potent (7×) but variable effect. many cells did not respond to naltrexone alone, but gave a significant response to combination treatment. Heisler et al. (Science 297(5581):609-11 (2002)) show that fenfluramine alone causes a 200% effect.

| Drug | Dose | Effect (%) | Drug | Dose | Effect (%) | Ratio |
|---|---|---|---|---|---|---|
| Naltrexone | 1 μM | 29650 | Naltrexone + Fenfluramine | 1 μM + 20 μM | 15080 | 0.51 |
| Naltrexone | 1 μM | 2200 | Naltrexone + Fenfluramine | 1 μM + 20 μM | 11440 | 520 |
| Naltrexone | 1 μM | 2500 | Naltrexone + Fenfluramine | 1 μM + 20 μM | 856 | 0.34 |
| Naltrexone | 1 μM | 417 | Naltrexone + Fenfluramine | 1 μM + 20 μM | 5700 | 13.67 |
| Naltrexone | 1 μM | 177 | Naltrexone + Fenfluramine | 1 μM + 20 μM | 430 | 2.43 |
| Naltrexone | 1 μM | 200 | Naltrexone + Fenfluramine | 1 μM + 20 μM | 2933 | 14.67 |
| Naltrexone | 1 μM | 700 | Naltrexone + Fenfluramine | 1 μM + 20 μM | | |

-continued

| Drug | Dose | Effect (%) | Drug | Dose | Effect (%) | Ratio |
|---|---|---|---|---|---|---|
| Naltrexone | 1 μM | 900 | Naltrexone + Fenfluramine | 1 μM + 20 μM | 1831 | 2.03 |
| Naltrexone | 1 μM | 2273 | Naltrexone + Fenfluramine | 1 μM + 20 μM | | |
| Naltrexone | 1 μM | 300 | Naltrexone + Fenfluramine | 1 μM + 20 μM | 920 | 3.07 |

What is claimed is:

1. A composition for affecting weight loss comprising a first compound and a second compound, wherein said first compound is an opioid antagonist selected from alvimopan, norbinaltorphimine, nalmefene, naloxone, methylnaltrexone, and nalorphine, and pharmaceutically acceptable salts thereof, and said second compound is selected from fluoxetine, fluvoxamine, sertraline, paroxetine, citalopram, escitalopram, sibutramine, duloxetine, and venlafaxine, and pharmaceutically acceptable salts thereof.

2. The composition of claim 1, wherein said opioid antagonist antagonizes an opioid receptor selected from a μ-opioid receptor (MOP-R), a κ-opioid receptor, and a δ-opioid receptor.

3. The composition of claim 1, wherein said opioid antagonist is nalmefene, or naloxone, or pharmaceutically acceptable salts thereof.

4. The composition of claim 3, wherein the second compound is fluoxetine or a pharmaceutically acceptable salt thereof.

5. A composition comprising:
a first compound selected from nalmefene, or naloxone, or pharmaceutically acceptable salts thereof; and
a second compound selected from fluoxetine, fluvoxamine, sertraline, paroxetine, citalopram, escitalopram, sibutramine, duloxetine, and venlafaxine, and pharmaceutically acceptable salts thereof.

6. The composition of claim 5, wherein the first compound is nalmefene or a pharmaceutically acceptable salt thereof.

7. The composition of claim 5, wherein the first compound is naloxone or a pharmaceutically acceptable salt thereof.

8. The composition of claim 5, wherein the second compound is fluoxetine or a pharmaceutically acceptable salt thereof.

9. A method of affecting weight loss, the method comprising administering the composition of claim 1 to an individual in need thereof.

10. The method of claim 9, wherein the individual has a body mass index (BMI) greater than 25.

11. The method of claim 9, wherein the individual has a body mass index (BMI) greater than 30.

12. A method of affecting weight loss, the method comprising administering the composition of claim 3 to an individual in need thereof.

13. The method of claim 12, wherein the individual has a body mass index (BMI) greater than 25.

14. The method of claim 12, wherein the individual has a body mass index (BMI) greater than 30.

15. A method of affecting weight loss, the method comprising administering the composition of claim 5 to an individual in need thereof.

16. The method of claim 15, wherein the individual has a body mass index (BMI) greater than 25.

17. The method of claim 15, wherein the individual has a body mass index (BMI) greater than 30.

* * * * *